United States Patent [19]

Bacus et al.

[11] Patent Number: 5,428,690
[45] Date of Patent: Jun. 27, 1995

[54] METHOD AND APPARATUS FOR AUTOMATED ASSAY OF BIOLOGICAL SPECIMENS

[75] Inventors: James W. Bacus, Hinsdale; James V. Bacus, Lombard; Robert E. Wagner, Chicago, all of Ill.

[73] Assignee: Becton Dickinson and Company, Franklin Lakes, N.J.

[21] Appl. No.: 837,051

[22] Filed: Feb. 18, 1992

Related U.S. Application Data

[63] Continuation-in-part of Ser. No. 764,336, Sep. 23, 1991, abandoned.

[51] Int. Cl.⁶ .............. G06K 9/00; G01N 33/48; G06F 15/00
[52] U.S. Cl. .................. 382/128; 356/39; 364/413.08
[58] Field of Search .......... 382/6; 356/39, 40; 364/413.07, 413.08, 413.13, 413.1; 422/65; 436/46; 359/391, 393; 358/93, 107

[56] References Cited

U.S. PATENT DOCUMENTS

| | | | |
|---|---|---|---|
| 3,805,028 | 4/1974 | Morton | 382/6 |
| 3,833,796 | 9/1974 | Fetner et al. | 356/39 |
| 3,851,972 | 12/1974 | Smith et al. | 356/39 |
| 4,122,518 | 10/1978 | Castleman et al. | 364/413.1 |
| 4,175,860 | 11/1979 | Bacus | 356/39 |
| 4,741,043 | 4/1988 | Bacus | 356/39 |
| 4,836,667 | 6/1989 | Ozeki | 359/393 |
| 5,018,209 | 5/1991 | Bacus | 382/6 |

*Primary Examiner*—Joseph Mancuso
*Assistant Examiner*—David Fox
*Attorney, Agent, or Firm*—Allen W. Wark

[57] ABSTRACT

An apparatus and method for automated assay of biological specimens positioned on microscope slides. The apparatus comprises an interactive optical subsystem for viewing the biological specimen on the slide and for producing an interactive video signal corresponding to the viewed image. An automated optical subsystem includes a single high power microscope objective for scanning a rack of slides, portions of which having been previously identified for assay in the interactive optical means. The system also includes a processor for processing the interactive and automatic video signals for the two optical subsystems. The processor receives the automatic video signal and performs biological assay functions upon it. A method and apparatus are also disclosed for marking points for later analysis on the microscope slides and for associating an analysis function with each marked point.

38 Claims, 19 Drawing Sheets

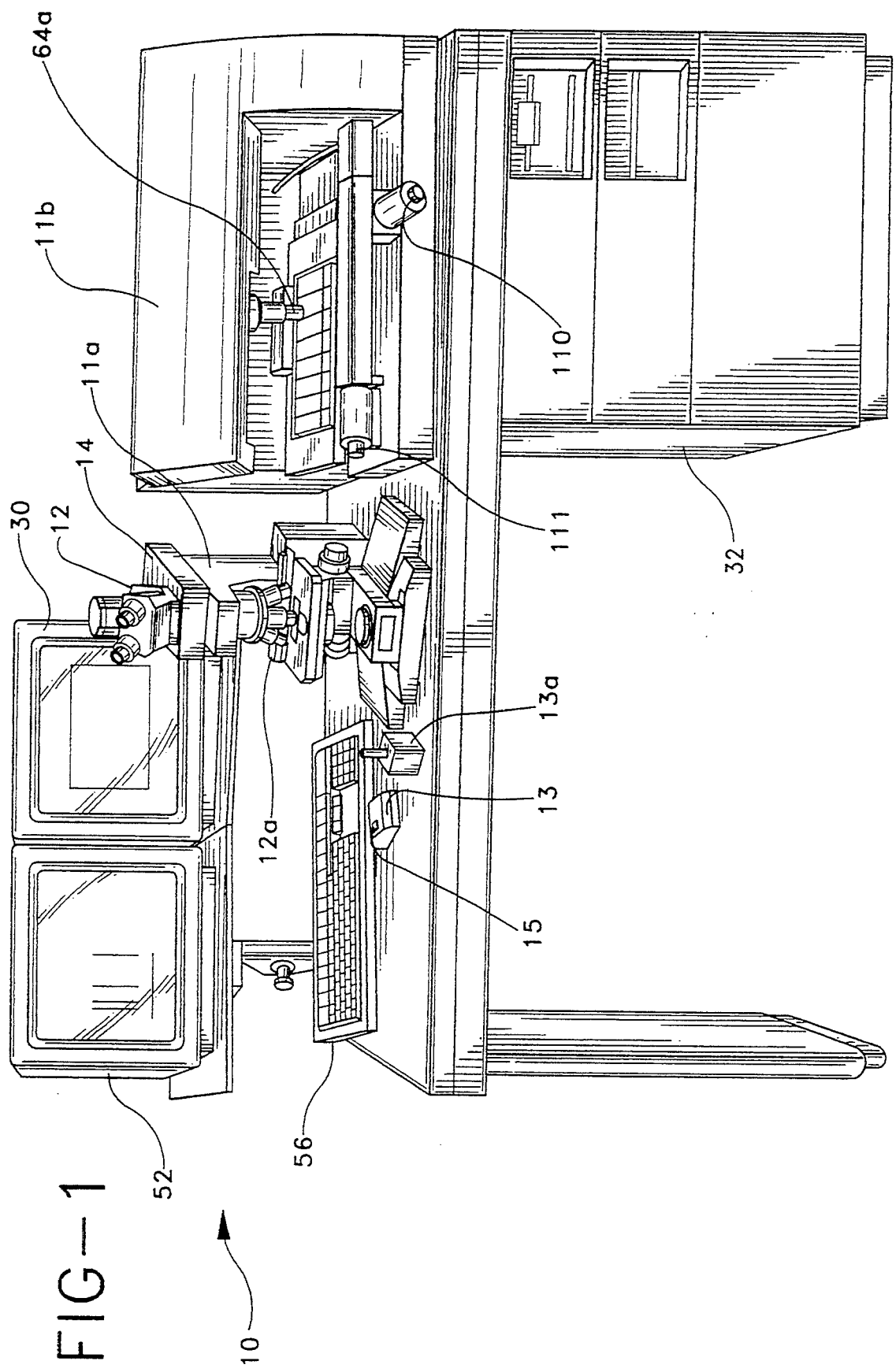

METHOD AND APPARATUS FOR AUTOMATED ASSAY OF BIOLOGICAL SPECIMENS

CROSS REFERENCE TO RELATED APPLICATION

This is a continuation-in-part of application Ser. No. 764,336 filed Sep. 23, 1991 to Bacus, et al., now abandoned.

BACKGROUND OF THE INVENTION

This invention relates to a system for performing an assay of slide mounted biological cell samples, and more particularly, for providing an automated method and arrangement to identify to the system locations at which to perform selected analysis functions.

The diagnosis and/or prognosis of a patient's condition frequently includes the removal of a cell sample, such as a tissue mass, from the patient. Although an attending physician may have good intuition regarding the patient's diagnosis and/or prognosis, confirmation of the diagnosis with histological examination of the cell sample removed from the patient is necessary. The histological examination entails cell staining procedures which allow the morphological features of the cells to be seen relatively easily in a light microscope. A pathologist, after examining the stained cell sample, makes a qualitative determination of the state of the tissue and reaches a conclusion regarding the prognosis for the patient. While this diagnostic method has a long history, it is somewhat lacking in scientific rigor since it is heavily reliant on the subjective judgment of the pathologist and it is extremely time-consuming.

The alternative to the strictly qualitative and time-consuming human analysis is automated cell analysis where the pathologist uses specialized equipment to perform the analysis. Flow cytometry equipment is one type of automated apparatus for cell analysis. With flow cytometry, mass tests are performed in gross on a specimen cell population without a researcher being able to exclude or include certain data of the population. The specimen is measured "as is" without really knowing what cells are being measured and how many. Important single cell data or data from relatively small groups of cells are lost in the overall averaging of a specimen. Further, relatively large amounts of a specimen have to be used to provide a required level of accuracy. Again, small changes in individual cells or small cell populations cannot be discerned.

Commercially available general purpose flow cytometers are very expensive and can handle only liquid blood specimens or tissue disaggregated specimens. Additionally, flow cytometers are incapable of working on standard tissue sections or using conventional microscope slides which are the preferred specimen forms of pathology laboratories.

Although the automation of cell analysis using microscope slide cell samples is exceedingly difficult, such has been automated to a human-machine interactive level. One such method and apparatus is described in U.S. Pat. No. 4,471,043 to Bacus, for Method And Apparatus For Image Analysis of Biological Specimens. Cell samples are attached to slides and an operator adjusts the system optics to view desired image fields of the cell sample. The operator then selects and classifies particular cell objects of the sample. After such operator action, the automated equipment quantitatively measures particular attributes of the selected and classified cell objects and records a digital representation of the optical image. The measured attributes can be reported on a per object basis or on an accumulated basis, and the stored image representations can later be read form memory for review.

Heretofore, slides prepared for use in image analysis often have different areas widely spaced on the slide at which different actions or functions are to be performed. For instance, a slide may have a clear area thereon which is selected for use in adjusting or calibrating the light and color levels needed for analysis of specimens located on the slide in another area of the slide. The operator may want to adjust the light level for each slide or for a group of slides in a slide tray or carrier. Also, the specimen cells may be located in a small portion of a specimen area on the slide and considerable time would be saved if the carrier positioned the slide specimen with this small portion of specimens directly beneath the microscope rather than having to examine large empty areas before locating the small specimen. Likewise, a calibration specimen in a calibration area may take a long time to locate by the machine because of the large empty area about the specimen. Still in other slides such as blood slides, the blood sample may cover the entire slide leaving no clear area for light setting.

The slides can be searched by the analysis apparatus to find particular areas, such as specimen or calibrate areas, however, doing so with a for example, 40× objective used for analysis, is difficult and time-consuming. The image area of a high power objective is only on the order of 20 by 20 microns so that each step in a search routine is very short and many such steps must be performed. Further, the depth of field with a high power objective is very short and refocusing must occur at each image field. When a clear area is under the slide, as will be the case for most of a search for small samples, much time is wasted trying to focus on non-existent objects. It is a significant problem in an automated analysis to be able to locate a small area or a specimen on a slide and to perform a desired function on each of a plurality of areas on the slides in a carrier in a fast and efficient manner.

SUMMARY OF THE INVENTION

In accordance with the present invention, an operator first performs a visual inspection of each slide noting the location of each area on the slide that an operator wants to perform a function. The operator then stores the address of the noted location and the associated function in a data file of the apparatus. The operator is assisted in identifying the areas on the slide by a coordinate system which may be in the form of a coordinate mask or pattern shown on or through the slide. By moving a computer monitor cursor to a point on a slide image, the address location of the point may be entered into the computer data file. Preferably, the operator may more finely define the coordinate address of the point by having an enlarged grid area shown on the monitor. The operator may then locate a spot on the enlarged grid to enter its coordinate location in the data file. The operator then enters the selected function for that location into the data file in association with the location. The operator proceeds to one or more locations on the same slide and enters a location and an associated function therefore for that slide. The operator proceeds with such a review for each slide of the group of slides in the carrier. After having considered each slide and associated a selected function for each selected location, the data file is completed. The carrier is then positioned in automated analysis apparatus for automatic analysis. The apparatus reads the data file and moves the carrier to have each slide and each location on each slide positioned beneath the microscope. The image analysis means performs the designated function at each location on each slide, and then slide-by-slide until all of the slides in the carrier have been automatically analyzed.

The invention includes an operator interactive method of and apparatus for easily finding very small things, such as a small dot or sliver of specimen, on a very large slide area that would be very difficult and time-consuming to locate automatically at the high resolution, e.g., 40× used when using an image analysis microscope. The slides used are transparent and the operator can easily see a zero, zero location point and a small sliver or dot of specimen, e.g., one centimeter in length or diameter in a large specimen area on the slide, e.g., a 5×20 centimeter specimen area. The field of the 40× microscope may be in the order of a 20×20 micron field and a large number of focusing repetitions and stepping of the stage and slide would be necessary to cover the empty areas if the specimen location were not located and addressed under low resolution by an operator previous to the slide being scanned automatically by the image analysis machine. The operator visually sees the specimen in a particular location on the slide and designates the section of the slide having the specimen and notes a marked position on that designated section as the coordinate address for the specimen. Preferably, the operator views a grid projected on the slide and designates the grid section having the specimen and such designation causes the grid section and specimen to be shown in enlarged size, e.g., 4× or 10× on a monitor screen. The mark noted by the operator may have been placed there by the pathologist at earlier time or the mark may be made by operator moving a mark along the monitor screen to a position adjacent the specimen while it is being viewed. In either event, the operator enters the address of the mark as the location to begin the scanning operation for the specimen. The preferred apparatus includes a flat bed carrier having a plurality of slides therein and the operator prepares each slide usually with several addresses and a specific function for the address such as focus, scan, analyze, etc. There may be more than one operator and more than one station that is pre-screening the slides interactively and the slides in their respective carriers are transferred to the automatic image analysis machine which automatically steps the flat bed carrier or a carrousel-type carrier to quickly move each slide through the various functions needed to perform the analysis.

BRIEF DESCRIPTION OF THE DRAWINGS

FIG. 1 is a perspective view of an apparatus for assaying biological specimens embodying the present invention;

DETAILED DESCRIPTION OF THE PREFERRED EMBODIMENT

The preferred embodiment disclosed herein is used for the assay or quantitation of biological specimens specifically estrogen and progesterone in tissue samples. The tissue sample staining and measuring techniques for the estrogen/progesterone assay are described in detail in U.S. Pat. No. 5,008,185, issued Apr. 16, 1991 to Bacus which is hereby incorporated by reference. The tissue sample assay is performed using a two-color optical system to enhance the optical characteristics of stained tissue samples. It will be apparent to those skilled in the art that many inventive features of the disclosed embodiment may be employed for other types of cell analysis e.g., DNA quantification and that other types of optical apparatus e.g., single color could be employed.

Figure 1A:
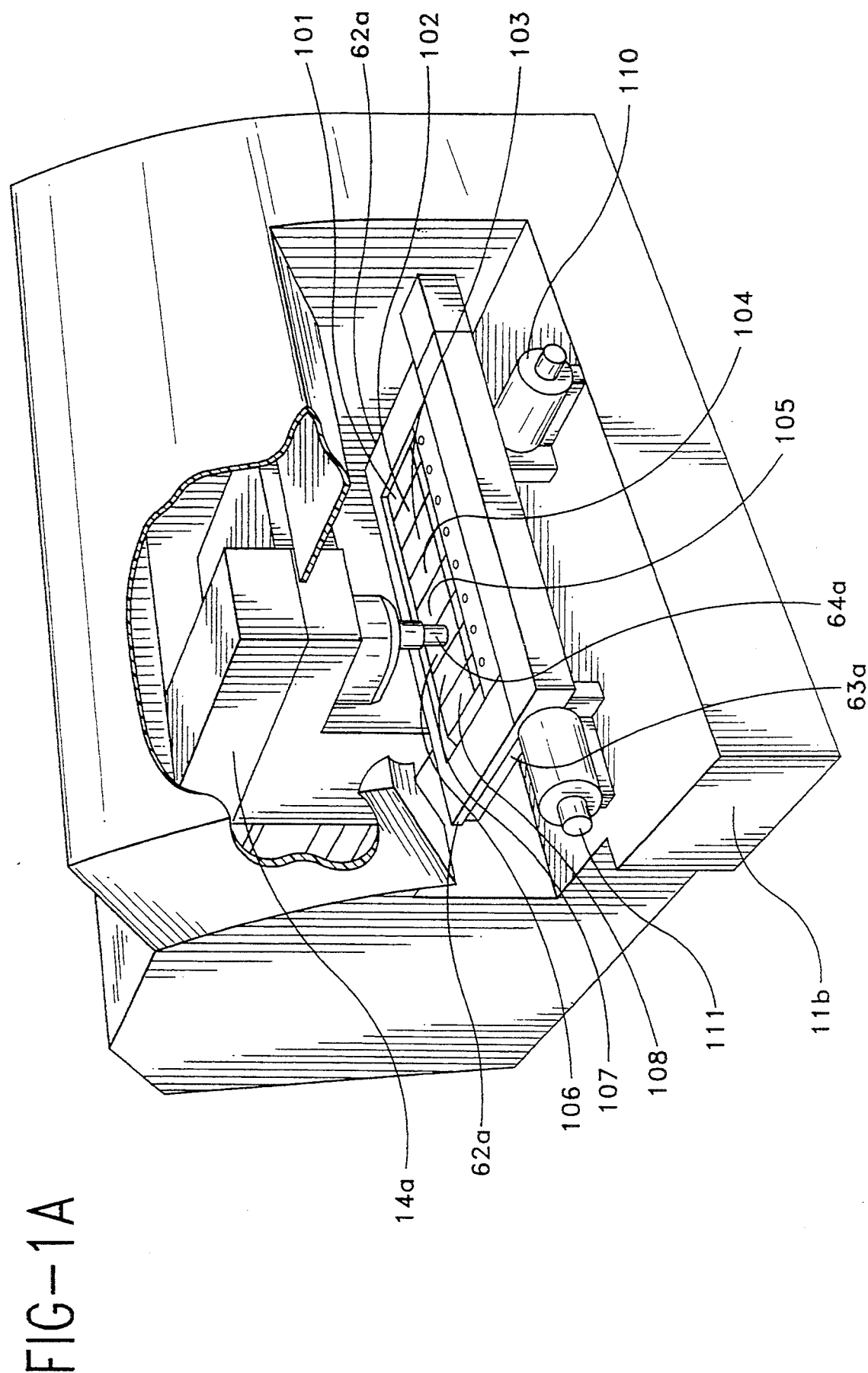
FIG. 1A is a perspective view, having portions broken away, of an automatic optical input subsystem of the apparatus for assaying biological specimens shown in FIG. 1.
Figure 2:
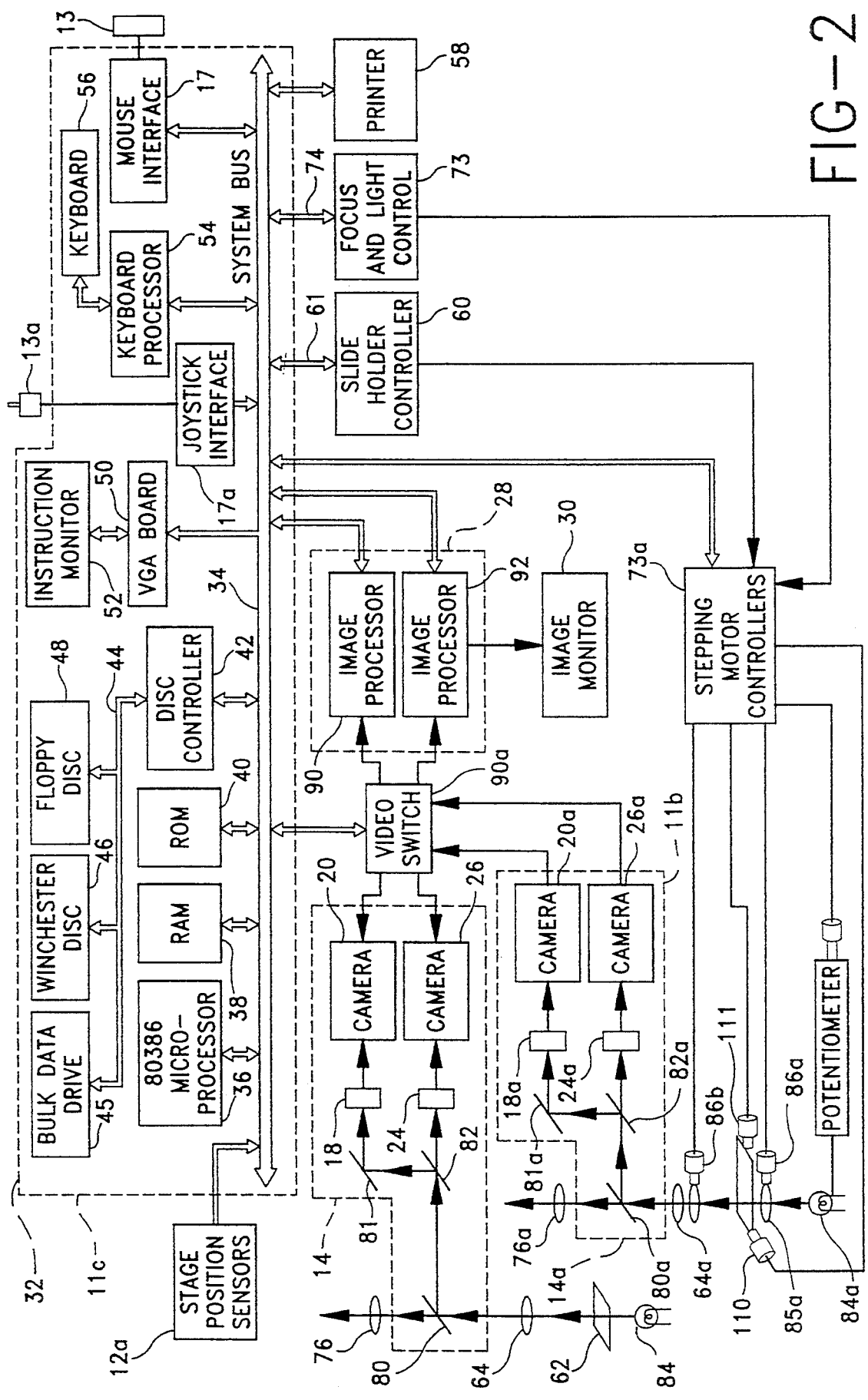
FIG. 2 is a block diagram of the apparatus shown in FIG. 1.

An apparatus for assaying biological specimens, and embodying the present invention and generally identified by numeral 10 is shown in perspective view in FIG. 1 and in block diagram form in FIG. 2. The apparatus 10 comprises an interactive optical input system 11a primarily for use in low power scanning of microscope slides of biological specimens to select fields for later analysis. An automated assay processing system 11b also comprises a portion of the apparatus for scanning up to eight slides at once at relatively high magnification for performing biological assays on the slide. A processor system 32 receives signals from the optical units for later image processing.

The interactive optical system 11a comprises an optical microscope 12, which may be of any conventional type, but in this embodiment, is a Riechart Diastar. An optical conversion module 14 is mounted on the microscope 12 to enhance the optically magnified image of cell samples viewed with the microscope 12. The optical conversion module 14, as may best be seen in FIG. 2, includes a beam-splitting prism 80 which conveys approximately 90% of the light into optical conversion module 14 and passes the remaining 10% to a microscope eyepiece 76. The light transmitted into module 14 is fed to a dichroic beam-splitter 82 which reflects a portion of the light to a television camera 20 via a red filter 18 and a mirror 81. The remaining portion of the light is filtered by a dichroic beam-splitter 82 and fed to a television camera 26 through a green filter 24. The dichroic beam-splitter 82 selectively passes light having wavelengths greater than approximately 560 nanometers to the filter 18 and having a wavelength of less than 560 nanometers to the filter 24. Thus, the dichroic beam-splitter 82 acts as a first color filter before the light reaches the color filters 18 and 24. Red filter 18 is a 620±20 nanometer bandpass optical transmission filter which provides a high contrast image to the camera 20. As shown in FIG. 2, the camera 20 then generates an NTSC image signal which is fed through an optical signal switch 90a to an image processor 90 of an image processor module 28 (FIG. 2). Green filter 24 is a 500±20 nanometer narrow bandpass optical transmission filter which provides a high contrast image to a camera 26. The camera 26 then feeds an NTSC image signal through the optical signal switch 90a to an image processor 92. Both of the image processors 90 and 92 contain analog to digital converters for converting the analog NTSC signals to a digitized 384 by 485 array pixel image. The center 256 by 256 array of pixels from this digitized image is then stored within frame buffers internal to the image processors 90 and 92. The visual image represented by the 256 by 256 array of pixels is referred to as an image field.

During assembly of the apparatus of FIG. 1, and from time to time thereafter, if necessary, the optical elements of conversion module 14 are adjusted so that each camera 20 and 26 receives the same optical image and each pixel of the digitized pixel arrays produced by processors 90 and 92, presents the same region of a viewed optical field.

Each of the image processors 90 and 92 is a Model AT428 from the Data Cube Corporation, and includes six internal frame buffers. The image processors 90 and 92 are connected to a system bus 34 of a computer 32. The frame buffers of image processors 90 and 92 are mapped into the address space of a microprocessor 36 in computer 32 to provide easy access for image processing. Additionally, an image monitor 30 is connected to image processor 92 and displays a cell sample image field stored in a predetermined one of the frame buffers. The storage of an image field representation into the predetermined frame buffer is described later herein.

The automatic optical conversion module 11b, as may best be seen in FIG. 2, includes a prism 80a which conveys the light into optical conversion module 14a. The light transmitted into module 14a is fed to a dichroic beam-splitter 82a which reflects a portion of the light to a television camera 20a via a red filter 18a and a mirror 81a. The remaining portion of the light is filtered by a dichroic beam-splitter 82a and fed to a television camera 26a through a green filter 24a. The dichroic beam-splitter 82a selectively passes light having wavelengths greater than approximately 560 nanometers to the filter 18a and having a wavelength of less than 560 nanometers to the filter 24a. Thus, the dichroic beam-splitter 82a acts as a first color filter before the light reaches the color filters 18a and 24a. Red filter 18a is a 620±20 nanometer bandpass optical transmission filter which provides a high contrast image to the camera 20a. As shown in FIG. 2, the camera 20a then generates an NTSC image signal which is fed through the optical signal switch 90 to the image processor 90 of the image processor module 28 (FIG. 2). Green filter 24a is a 500±20 nanometer narrow bandpass optical transmission filter which provides a high contrast image to a camera 26a. The camera 26a then feeds an NTSC image signal through the optical signal switch 90a to the image processor 92.

The microprocessor 36 of computer 32 is an Intel 80486 microprocessor which is connected to the system bus 34. The optical switch 90a, under control of the microprocessor 36, selects the signal from interactive unit 11a or automatic unit 11b to be fed to the image processors 90 and 92. A random access memory 38 and a read only memory 40 are also connected to the system bus 34 for storage of program and data. A disk controller 42 is connected by a local bus 44 to a Winchester disk drive 46 and to a floppy disk drive 48 for secondary information storage. Advantageously, local bus 44 is connected to a moveable media bulk data drive 45 such as an optical write once read many times (WORM) drive for image field recording and retrieval.

A video conversion board 50, in this embodiment a VGA board, is connected to the system bus 34 to control an instruction monitor 52 connected to the VGA board 50. Operational information such as selection menus and reports of analysis are displayed on instruction monitor 52. A keyboard processor 54 is connected to the system bus 34 to interpret signals from a keyboard 56 connected to the keyboard processor 54. Input signals to microprocessor 36 are also generated by a hand control drive (mouse) 13 having a control button 15. Signals from mouse 13 and its button 15 are conveyed to bus 34 via a mouse interface 17. A printer 58 is connected to the system bus 34 for communication with microprocessor 36. The apparatus 10 also includes a joystick control device 13a of a type well known in the art. Signals from the joystick 13a are conveyed to bus 34 via a joystick interface 17a.

The automated image input subsystem 11b of apparatus 10 performs automated X-Y slide positioning, image focusing, light intensity adjustment and light color balancing functions. The X-Y slide position controlling apparatus is shown in FIGS. 1, 1A, 3 and 4, and includes a slide holder 62a capable of holding eight microscope slides 101 through 108 in side-by-side relationship such that the upper surfaces of the slides are substantially coplanar. Slide holder 62a, which is sometimes referred to as a flat bed carrier, is movably attached to the stage 65a of microscope objective 64a by means of a slide holder base 63a. The portion of slide holder 62a positionable with respect to microscope objective 64a is controlled by an X position stepper motor 110 and a Y position stepper motor 111 which are mechanically attached to base 63a. The stepper motors 110 and 111 are of the type known in the art which respond to pulse signals from a slide holder position controller 60. The actual X and Y positions of the slide holder 62a are sensed by an X position sensor 68 and a Y position sensor 66, respectively, which substantially continuously report position information to slide holder controller 60. In the present embodiment the slide holder 62a, base 63a, and position sensors 66 and 68 including limit switches and numbered 110 and 111 comprise a commercially available unit from Marzhauser Wetzlar GmbH Model EKSB-S4 with Model MCL-3 control units.

Responsive to appropriate stepper motor control signals, the slide holder base 63a is capable of placing substantially all of each of slides 101 through 108 under the objective 64a. Slide holder position controller 60 is connected to system bus 34 by means of a communication path 61. Microprocessor 36, as discussed later herein, transmits commands to slide holder position controller 60 specifying an X and Y position to place under the microscope objective 64a. Slide holder position controller 60 responds to such commands by transmitting to the X and Y stepper motors 110 and 111 the appropriate sets of pulse signals to move the slide holder 62a to the desired X-Y position. The actual position of slide holder 62a is checked by slide holder position controller 60 during and at the completion of movement. The slide holder position controller 60 also maintains an internal record of the X and Y position of the slide holder 62a which internal record can be read by microprocessor 36 via bus 34 and communication path 61.

Figure 4:
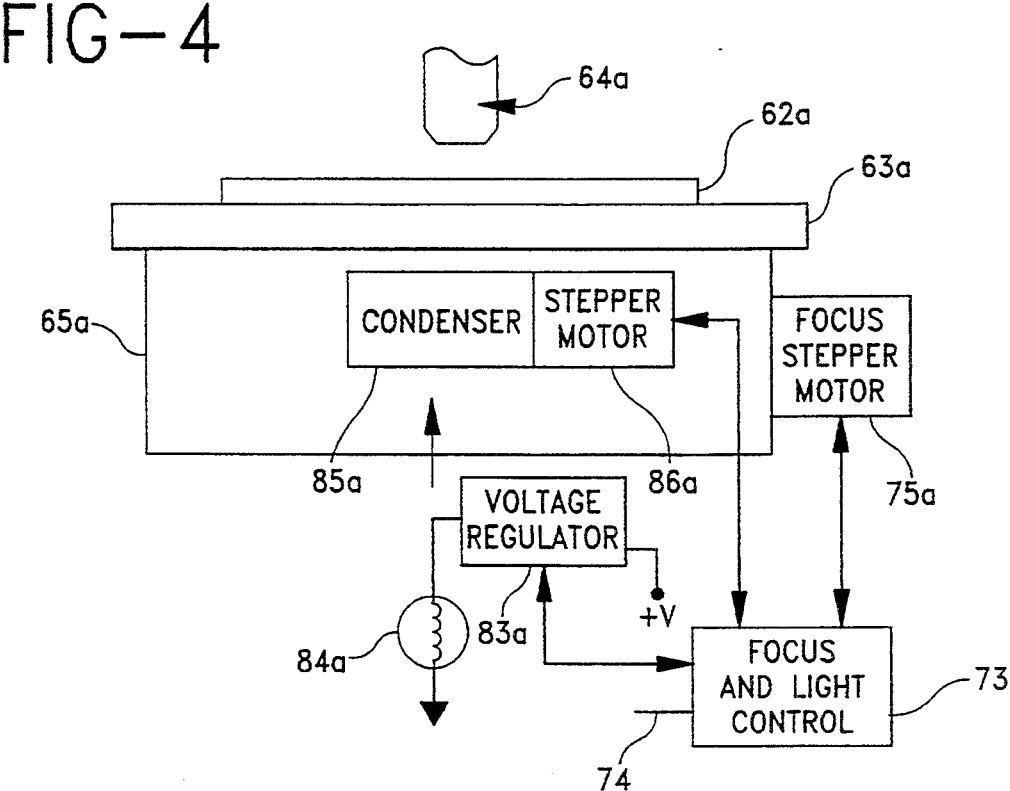
FIG. 4 is a block diagram view of focus and light control portions of the apparatus shown in FIG. 1.

The apparatus 10 also includes a focus and light controller 73 which controls the light intensity and color balance from the light source 84a, as well as the focus of the image field presented to microscope 12. Microprocessor 36 communicates with focus and light controller 73, via the system bus 34 and a communication path 74, to control the focus and light properties. FIG. 4 is a functional block diagram of focus and light controller 73 and its connection to objective 64a and to bus 34. The objective 64a includes a focus stepper motor 75a, which is controlled by focus and light controller 73 through the stepper motor controller 73a to raise and lower the stage 62a, and thereby raise and lower the microscope slides 101 through 108 carried by slide holder 62a. Microprocessor 36 includes a focus routine which is periodically performed during tissue analysis. When the focus routine is entered, microprocessor 36 reviews a digital representation of an image field from the image processors 90 and 92, and issues a command to focus and light controller 73, to raise or lower the stage by a specified amount. Focus and light controller 73 responsively transmits to focus stepper motor 75a electrical signals to implement the requested stage movement. By continued checking of the quality of the image field and adjustment of the up and down position of the slide holder 62a, microprocessor 36 brings the upper surface of the slide under the objective 64a into focus.

Microprocessor 36 also stores a target value for the light intensity which is to be maintained during tissue sample analysis. This stored light intensity value is used by microprocessor 36 in conjunction with an intensity function to regulate the intensity of light from light source 84a. When the intensity function of microprocessor 36 is enabled, the light intensity as represented by image fields from image processors 90 and 92 is determined. Any departure from the stored target light intensity value is corrected by sending intensity control commands to focus and light controller 73 which responds thereto by controlling a voltage regulator to increase or decrease the voltage applied to light source 84a. Voltage regulator 83 may be, for example, a standard rotatable voltage regulator which is rotated by a stepper motor operating under the control of electrical signals from focus and light controller 73.

The analysis performed in the present embodiment relies on a two-color system. For accuracy of measurement, it is important that the two-colors observed by cameras 20 and 26 be of substantially the same intensity. The microprocessor 36 includes a color balance function, which is called to match the intensities of the red and green colors applied to cameras 20 and 26 by light source 84. Objective 64a has associated with it a condenser 85a, which is controlled by a stepper motor 86a, electrically connected to focus and light controller 73. When in the color balance function, microprocessor senses color imbalance by comparing the image field of image processor 90 with that of image processor 92. Microprocessor 36 sends color balance adjustment commands to focus and light controller 73 in response to color imbalance and through a process of repeated comparison and color balance adjustment commands achieves a color balance suitable for tissue sample analysis.

Figure 5:
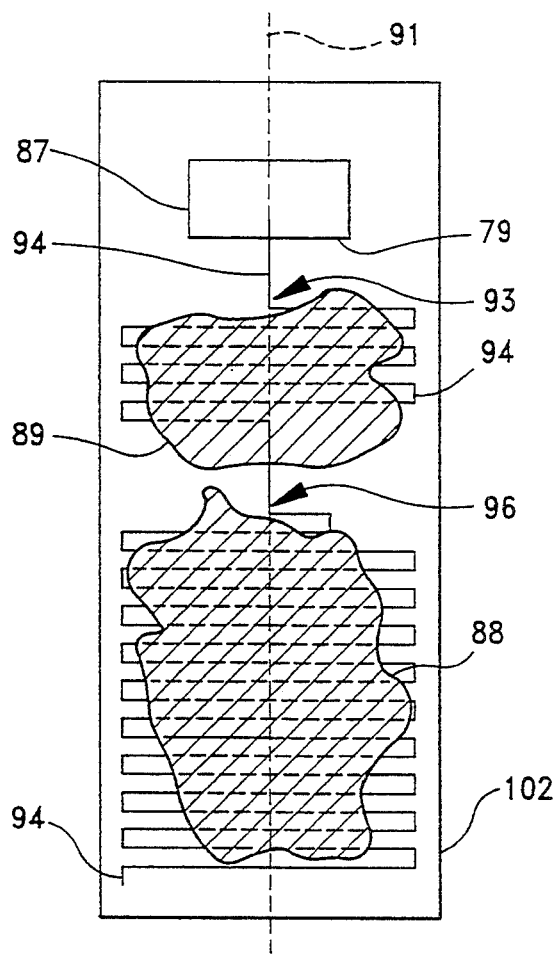
FIG. 5 is a plan view of a tissue section microscope slide for use with the apparatus of FIG. 1.

FIG. 5 shows a representation slide e.g., 102 which has been prepared for analysis in accordance with the embodiment. The slide 102 includes a dark line outline 87 of a rectangle near one end thereof. The rectangle 87, which is printed in substantially the same position on all slides is used during focus and light adjustment routines and during slide preparation to identify the placement of tissue samples.

A method of quantitating nuclear proteins of the present embodiment includes providing specimen 88 cell objects on slide 102 and staining them with an optical enhancement factor which specifically binds to the nuclear protein. The stain is then viewed with the image analysis system 10 to measure the optical density of the stain for intensity measurement and to locate the areas in which stain is found for distribution measurement. Because the intensity of the staining relates to the quantity of the nuclear proteins, measurement of the different optical densities of the stain permits a direct measurement of the quantity of the proteins. In the preferred embodiment, control cell objects 89 are placed on a reference section of the slide 102 to provide a normalization or reference optical density for the staining. Further, one or several counterstains can be used to further distinguish among several features of the cell objects.

No actual marks except rectangle 87 appear on the slides 101-108 to differentiate the control cell objects 89 from the specimen 88. However, for automated location of points to begin analysis, the slide should be prepared such that the control cell objects 89 overlap the longitudinal center line of the slide (denoted by a dotted line 91 in FIG. 5) and that the control cell objects 89 are closer to the rectangle 87 than is the specimen 88. Similarly, the specimen 88 should be positioned overlapping the longitudinal center line and farther from rectangle 87 than the control cell objects 89.

Figure 7:
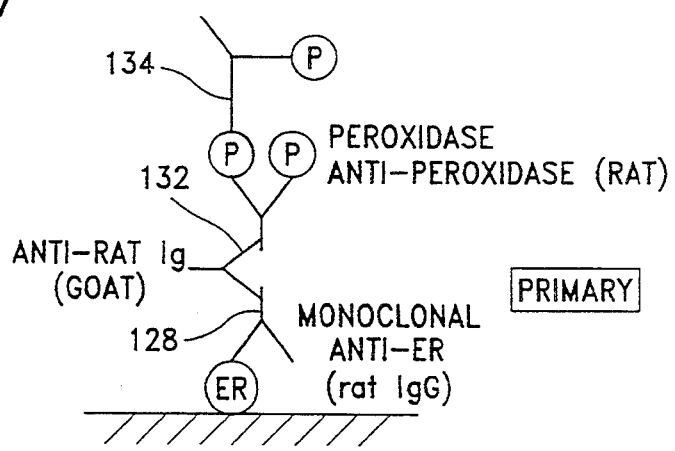
FIGS. 7 and 8 are schematic views of the biological specimen preparation prior to assay.
Figure 8:
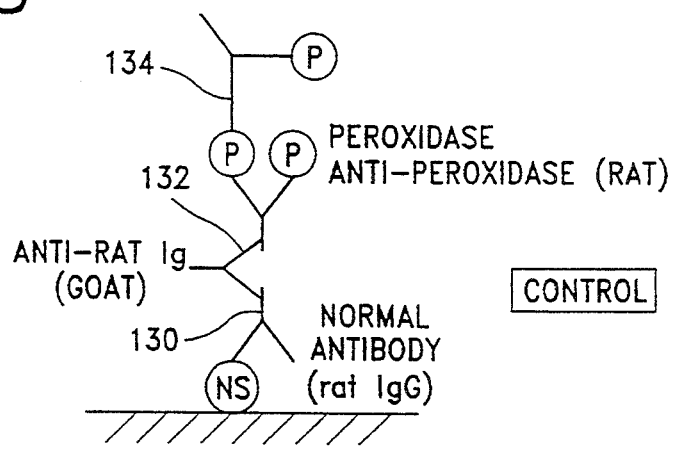

Preferably, in one particular embodiment, the staining method employs a sensitive peroxidase-antiperoxidase technique for visualization of estrogen or progesterone receptors in specimens through the use of monoclonal antibodies directed specifically against those receptors. A diagrammatic representation of the process on the microscopic level is illustrated in FIGS. 7 and 8. Two portions of a human tumor specimen containing a cell population from which the estrogen receptors are to be measured are placed on the two separate sections of the slide 14 and suitably fixed thereto as by tissue adhesive. The separate sections are then fixed in separate washes of formalin, methanol and acetone, and thereafter, treated with a blocking reagent to prevent non-specific binding of the subsequent reagents.

The part of the specimen cells 88 to be measured is incubated with a primary antibody, a monoclonal antibody (rat) to human estrogen receptor in the specimen portion of the slide. This antibody, as represented at 128, binds specifically to the estrogen receptor sites ER of this tissue portion. The reference portion 89 of the specimen is incubated with a control, normal rat IgG, represented at 130. The purpose of the control 130 is to evaluate the amount of binding of the immunoperoxidase reagents in this technique to nonspecific sites NS of the specimen to yield a background measurement.

Both tissue sections 88 and 89 on the slide 102 are then incubated with a bridging antibody, an anti-rat immunoglobulin (goat) illustrated at 132 in both figures. The bridging antibody 132 binds to the rat antibody 128 against human estrogen receptor in the specimen section 88 and to any bound normal rat IgG 130 in the control section 89.

A rat PAP complex 134 is added to both sections 88 and 89 of the specimen and binds to the anti-rat IgG bridging antibody at 132. After this step, a solution containing hydrogen peroxide and diaminobenzidine (DAB) and 4 N HCl is added to the specimen and control sections. The reaction of the peroxidase with hydrogen peroxide converts the bound DAB present into an insoluble reddish brown precipitate. The proportion of the precipitate and its location are influenced by the binding positions of the PAP complex and, through the bridging and primary antibodies, the locations and amounts of the estrogen receptors in the specimen.

The concentrations, timing, and chemical compositions of the reagents used in this staining method are more fully described in the aforementioned U.S. Pat. No. 5,008,185. Preferably, the monoclonal antibody which is used to bind to the estrogen receptor sites is one of those developed at the University of Chicago and designated H222 sP2 and H226 sP2, and that which is used to bind to the progesterone receptor is one which is commercially available from Transbio Sarl 6 Rue Thiers, Paris France and designated mPRI.

The DAB precipitate is then visualized by image analysis with apparatus 10 to determine the quantitation of the estrogen receptors in the specimen. In general, the brown precipitate does not transmit light well and will show up as dark areas in the cells of the specimen. The optical density and hence pixel intensity will be related directly to the amount of DAB precipitate and to the quantity of estrogen receptor which has bound the antibodies. To be able to more clearly visualize the nuclear area of each cell, a counterstain of methyl green is added. It is important to note that both the primary stain of DAB precipitate and the counterstain of methyl green are specific to the nucleus of each cell. This means that debris and other cellular features will appear lighter in the microscope image and can be distinguished.

A dual camera method is thereafter applied to distinguish the areas stained by the DAB and the areas stained by the methyl green. The red and green filters 18 and 24 respectively form monochromatic images of the cell objects at their respective cameras 20 and 26 which images can be stored in the apparatus 10. These images, one by the red filter and the other by the green filter, are used to separate the primary stained areas from the nuclear areas, and to separate the nuclear areas from other cell or field features.

Figure 6:
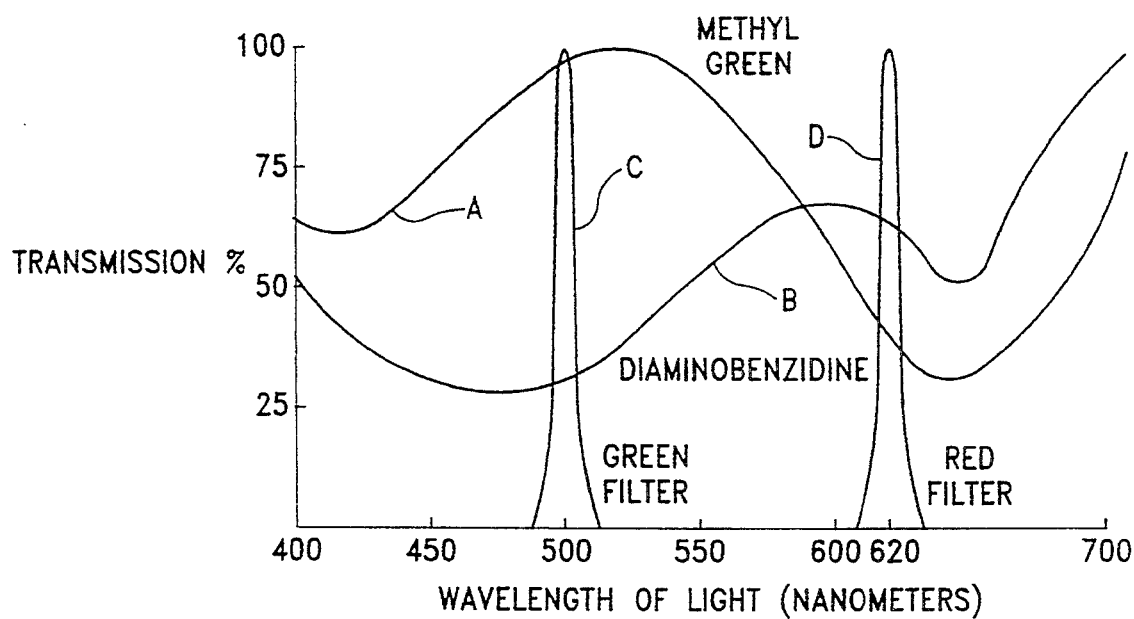
FIG. 6 is a graphical representation of the optical properties employed in biological specimen assay.

The results and desirability of this dual filtering of a counterstained cell image are more fully illustrated in FIG. 6. The percentage of light transmitted through the nuclei stained with methyl green is shown in the curve A as a function of the wavelength of light. The percentage of transmission of light for diaminobenzidine (DAB) is shown in curve B as a function of the wavelength of light. The bandwidth of wavelengths of light passed by the green filter is illustrated in band C while the bandwidth of wavelengths of light passed by the red filter is illustrated in band D.

When an image of a counterstained cell population or specimen is filtered with the green filter 24, substantially all of the areas stained with the methyl green will be invisible. This is because the methyl green curve A has a relative transmissive peak near this wavelength band while the diaminobenzidine curve B is relatively non-transmissive in this band. Thus, the areas with primary DAB stain can be separated from the nuclear areas. At the other extreme of the graph, the band D of the red filter is positioned at a place where just the opposite occurs. The methyl green curve A has a relatively non-transmissive valley in this bandwidth while the diaminobenzidine curve B is also relatively non-transmissive. Thus, the nuclear areas containing both the primary stain and the counterstain appear darker than other cell features and can be readily identified.

Because of the relative differences in light transmission between the primary and counterstain in the two filtered bandwidths, the methyl green stained area is enhanced during one filtering relative to other areas of the cell, and the areas which have diaminobenzidine precipitate are enhanced relative to the methyl green areas during the other filtering. Thus, the nuclear areas of the cell objects are optically enhanced along with the areas having DAB precipitate.

Figure 11:
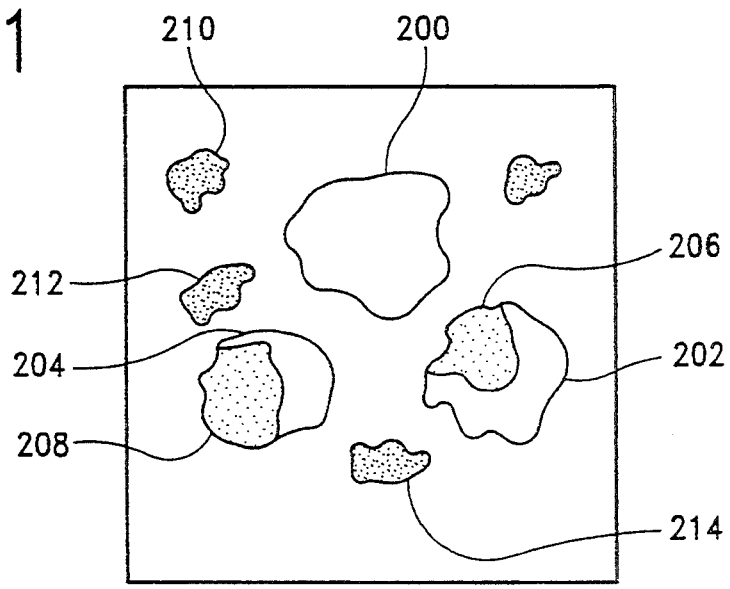
FIG. 11 represents an image field of an optically unfiltered tissue section.
Figure 12:
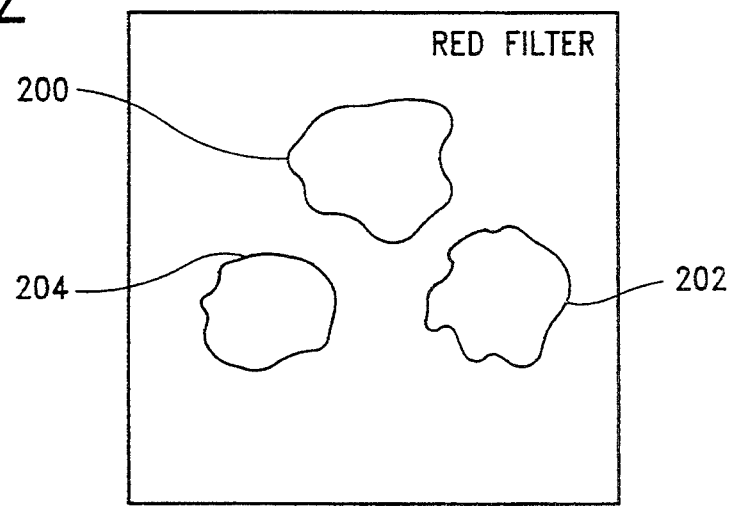
FIG. 12 represents the image field of FIG. 11 when optically filtered by a red filter having a passband centered about 620 nanometers.
Figure 13:
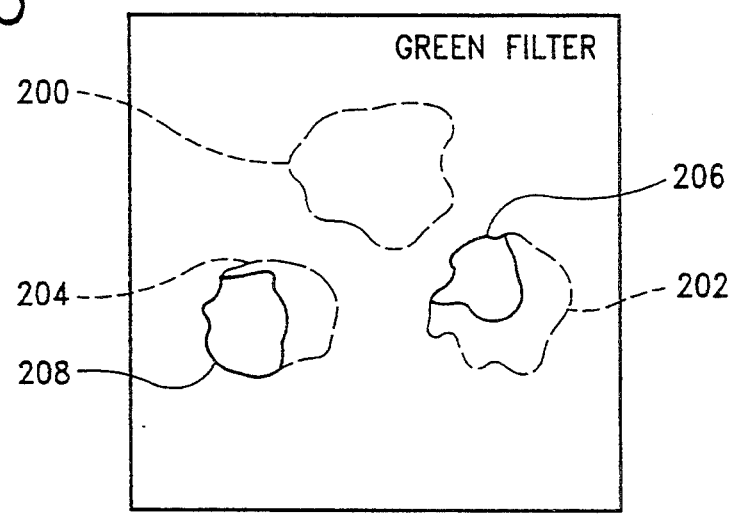
FIG. 13 represents the image field of FIG. 11 when optically filtered by a green filter having a passband centered about 500 nanometers.

FIG. 11 represents an optical image field of a tissue sample as presented to the microscope objective 64. In the image of FIG. 11, objects 200, 202 and 204 are green cell nuclei where nuclei 202 and 204 have brown areas 206 and 208 respectively of DAB precipitate. Nucleus 200 does not contain any estrogen receptor and therefore, does not have any DAB precipitate. Objects 210, 212 and 214 are various other cell features or debris from the tissue section. FIG. 12 represents the image field presented by red filter 18 to camera 20 and its associated image processor 90. In FIG. 12, the nuclei 200, 202 and 204 stand out because of the counter staining and filtering, while the DAB areas are not visible. FIG. 13 represents the image field presented by green filter 24, to camera 26 and its associated image processor 92. In FIG. 13, the estrogen receptor areas 206 and 208 stand out so that their area and density can be readily measured. The dotted lines of FIG. 13 represent the boundaries of nuclei 200, 202 and 204, which are shown for reference purposes. As previously discussed, a monitor 30 is available for displaying image fields of the cell sample. When an image field is to be displayed, microprocessor 36 computes a composite image by summing the image field of image processor 90 (of the type shown in FIG. 12). With the image field of image processor 92 (of the type shown in FIG. 13), the composite image is then stored by microprocessor 36 in the predetermined frame buffer of image processor 92 which is the source of images for monitor 30.

While the implementation shows a convenient and advantageous method for discriminating between the two areas having counterstaining, it is recognized that there are various other staining or optical enhancement methods and filtering methods which can be used to optically enhance one particular area or feature over another cell feature. For the quantitation of the specific hormonal receptors shown (progesterone and estrogen receptors), what is important is to distinguish the nuclear area which contains receptors by the presence of the diaminobenzidine precipitate.

In the preferred embodiment, up to eight slides mounted in a slide tray are analyzed in an automatic analysis session. One of the eight slides (101) is a calibrate slide and the remaining seven slides are preferably prepared using tissue sections from the same tissue mass. The calibrate slide 101 is prepared in the same manner as all other slides, but the tissue sections used are taken from a standard tissue mass having known amounts of estrogen and progesterone receptors. Preferably, all eight slides which are to be analyzed in the same session are fixed and stained in accordance with the above disclosed process as a batch, so that they all undergo substantially the same preparation.

Figure 3:
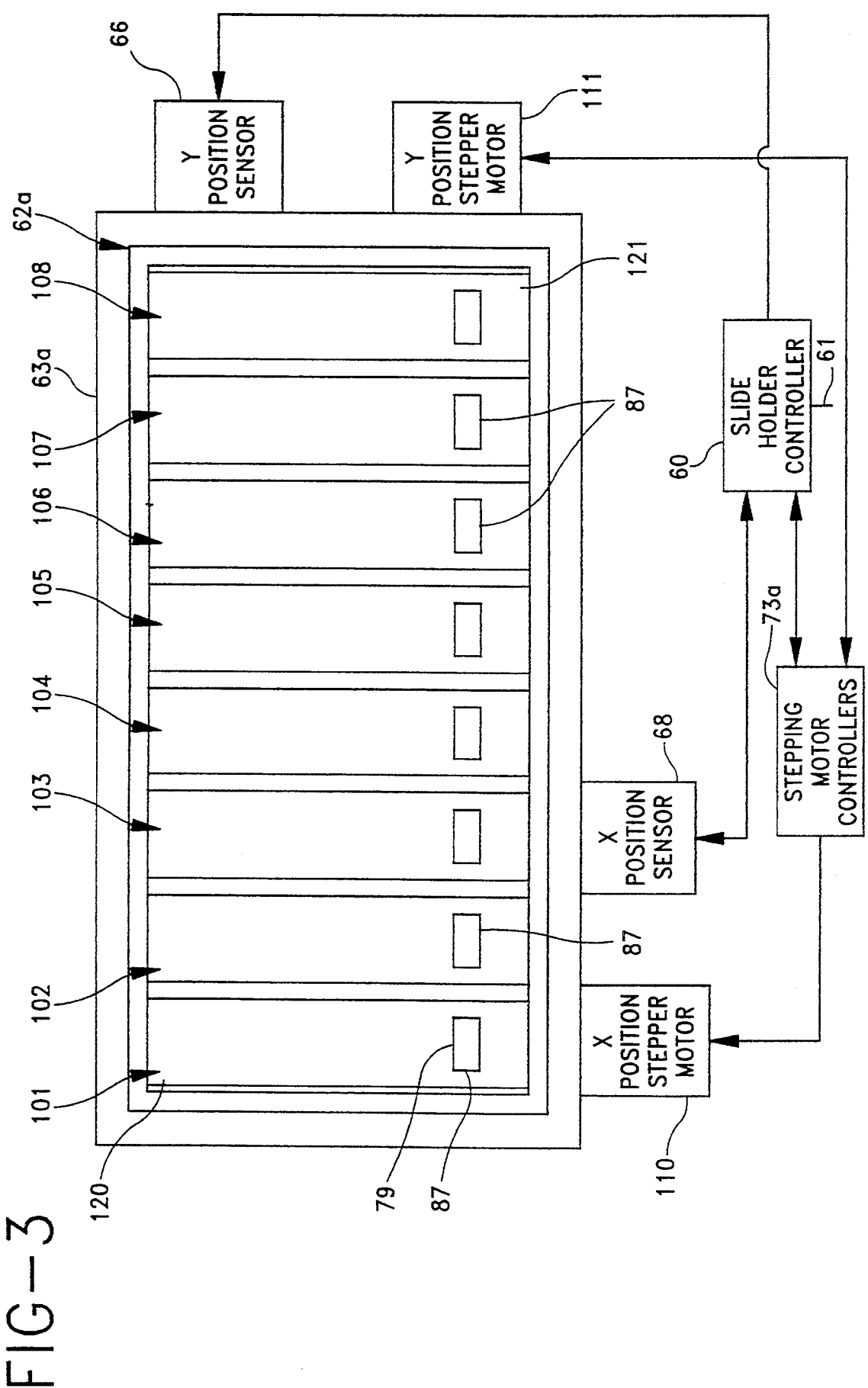
FIG. 3 shows a slide holder and associated control equipment of the apparatus shown in FIG. 1.

Upon completion of the fixing and staining of the slides 101 through 108, they are inserted into slide holder 62a which secures each slide at a predetermined position on the slide holder. In the present embodiment, calibration slide 101 is placed in the left most position and the slides 102 through 108 are distributed in any order in the remaining seven slide positions. All slides are oriented so that their printed rectangle 87 is at the bottom as shown in FIG. 3. The slide holder is then inserted into the slide holder base 63a with the printed rectangles away from microscope 12. After placement of the slide holder, the operator signals, by means of keyboard 56, that the analysis is to begin.

Figure 9:
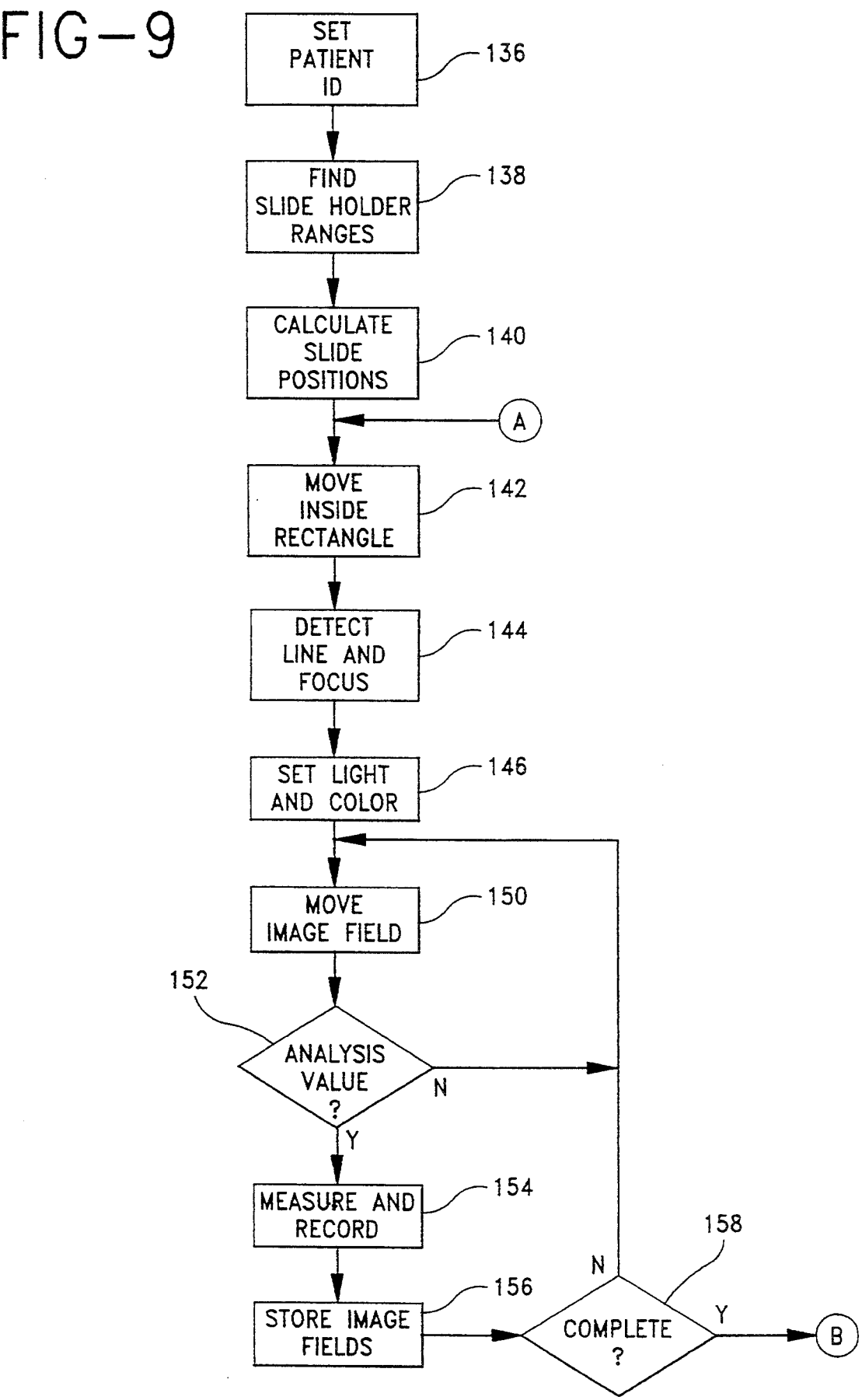
FIGS. 9 and 10 are flow diagrams of the control procedures invoked in the assay of a plurality of biological specimens.
Figure 10:
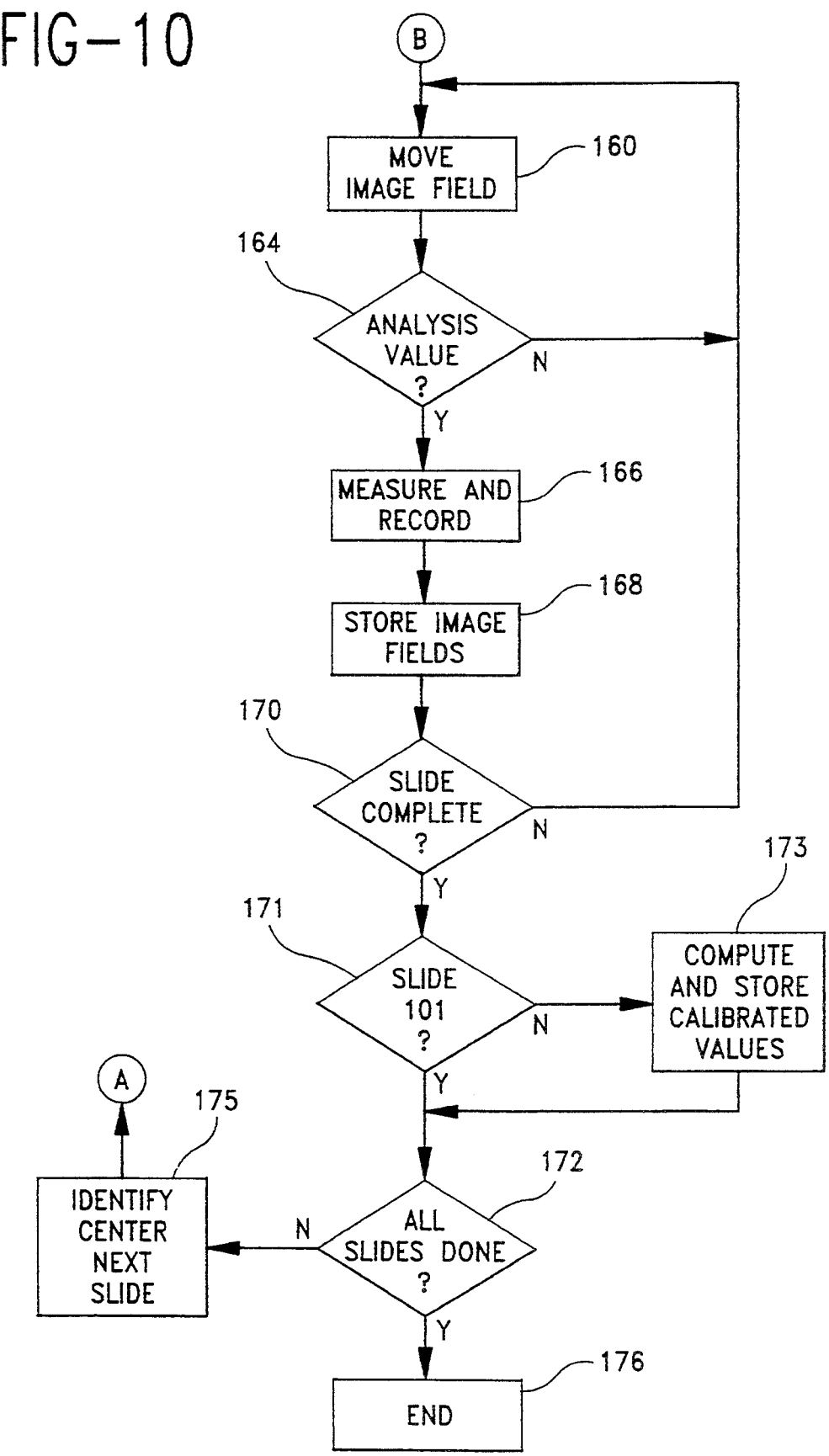

A flow diagram of the automated analysis routine is shown in inter-related FIGS. 9 and 10. The routine begins at a step 136 with a request by the apparatus on instruction monitor 52 for patient labelling information. When patient labelling is completed by means of operator interaction with the keyboard 56, the automated portion of the analysis procedure begins and the operator is free to go about other tasks.

Initially, microprocessor 36 by means of control signals sent over system bus 34 to the slide holder position controller 60, requests the movement of slide holder 62a to its maximum X and Y positions, as represented by a point 120 in the upper left of slide 101 and a point 121 in the lower right of slide 108. No actual marks appear on the slides to represent points 120 and 121, but these points are located by the maximum travel of the slide holder 62a. The X and Y values of points 120 and 121 are read from position sensors 110 and 111 so that the position ranges of slide holder 62a are known by microprocessor 36. Since the slides 101 through 108 are held in predetermined positions, microprocessor 36 can easily compute the X address of the longitudinal center of each slide 101 through 108, and since the position of the rectangle 87 on each slide is also known the Y position of each rectangle 87 can be computed with reasonable accuracy. These slide reference positions are calculated in step 140. The analysis routine next proceeds to step 142 in which the microprocessor 36 requests movement of the slide holder 62 to position the near center of rectangle 87 of slide 101 under the objective 64a.

The automated analysis routine of the present embodiment is performed using a single 40× objective which has a short depth of field on the order of a few microns. Although the slide holder and slides are relatively precise, they do not necessarily guarantee that the surface of the slides will always be at optimum focus when presented to the microscope objective 64a. Accordingly, as the analysis for each new slide begins, the apparatus is first focused using a line 79 of the slide rectangle 87. After the initial focus on line 79 is achieved, the apparatus is periodically refocused during analysis to provide accurate image fields.

In a step 144, the slide 101 is moved so that the path of the objective travels along the imaginary center line 91 (FIG. 5) until line 79 is detected. Line 79 is of sufficient width and opacity that it is detectable even with a poorly focused objective. As the slide 101 moves, microprocessor 36 monitors the pixel array of image processor 90 which represents the current image field presented to the objective. Microprocessor stops slide movement, when line 79 appears in the image field of image processor 90 and performs a focus routine on the inner edge of line 79. In the focus routine microprocessor 36 successively analyses the sharpness of the image field from image processor 40 and adjusts the microscope stage to objective distance by means of focus and light controller 73. When accurate focus is detected by microprocessor 36, the flow proceeds to block 126 in which the slide is moved back to a point within rectangle 87. The rectangle 87 is to be free from any tissue section or other contaminants. Accordingly, the light level and color balance can be adjusted by means described above while the presented image field is from within rectangle 87.

After light level and color balance are established the routine proceeds to a step 150 in which the slide is moved to view successive image fields along the center line 91 in search of a first image field representing reference tissue sample 89. The slide is moved so that the objective 64a traces a path represented by a search path line 94 shown in FIG. 5. Periodically slide motion is stopped, the objective 64a is focused by the microprocessor 36 and the then current image field from image processor 90 is analyzed to determine if the control sample has been found. An image field of control sample 89 will be identified in a step 152 as an image field possessing analysis value. An image field is determined in step 152 to possess analysis value when the area of the nuclear material in the image field from image processor 90 exceeds a predetermined threshold stored in microprocessor 36. Microprocessor 36 analyzes each image field pixel array from image processor 90 which arrays represent the nuclear image of the image fields. When the nuclear area of an image field exceeds the threshold stored in microprocessor 36, the image field has analysis value and the flow proceeds to step 154 where attributes of the image field are measured and recorded.

In step 154, the digitized image field from image processor 90 is analyzed to identify a nuclear boundary level value for the nuclear material in the field. The nuclear boundary level which will be used in quantitation of the specimen 88 is stored in memory 38. Also, in step 154 microprocessor 36 measures the digitized image field from image processor 92 to identify an antibody stain threshold. This threshold is necessary to determine the contribution of the non-specific staining of the control cells and the contribution of the counterstain methyl green, to the total stain detected by the instrument. This antibody stain threshold permits the discrimination between antibody negative stain cells and antibody positive stain cells. After its determination, the antibody stain threshold level is stored in memory 38. Upon completion of the measurement and recording of step 154, a step 156 is performed in which the digital image fields of both image processors 90 and 92 are stored in memory. The digital image fields may advantageously be stored in bulk data drive 45.

The search path 93 (FIG. 5) begins within rectangle 87 and proceeds along center line 91 until a first image field having analysis value is detected at point 93. When microprocessor 36 detects the first control cell object image field, the search movement pattern, directed by microprocessor 36, changes the search movement pattern for image fields, as directed by microprocessor 36, follows a sweeping pattern back and forth across the control as represented in FIG. 5 by the line 94. While traversing the reference specimen 89 successive image fields of the specimen are analyzed and for each image field the possessing analysis value, the nuclear boundary level and the antibody stain threshold are updated. Also, both digital images of each image field found to possess analysis value are stored in memory. Image fields continue to be analyzed from control specimen 89 until the total nuclear area of the image fields of analysis value exceeds 5,000 square microns. When the 5,000 square micron threshold is detected in step 158, slide holder movement is directed to return the objective 64 to center line 91 and to proceed downwardly (step 160) until a first specimen image field is detected at point 96 of FIG. 5. In a manner similar to step 152, the image field having analysis value is identified in step 164 of the flow diagram (FIG. 10) based on the nuclear area contained by the image field.

When step 164 finds an image field having analysis value, the flow proceeds to step 166 where attributes of the specimen image field are measured and recorded. The attributes measured and recorded in step 166 comprise the optical density of DAB areas 206 and 208, the visible area of DAB areas 206 and 208 and a comparison of the total nuclear area in the image field with the area of DAB areas 206 and 208. After measuring and recording image field attributes in step 166, the digitized representations of the image field are also stored in memory. In the present embodiment, the entirety of the specimen 88 is scanned by the apparatus as represented by the line 94 (FIG. 5). The completion of scanning for tissue sample 88 is detected in step 170.

When, as is the case in the present example, the recorded data relates to calibration slide 101, as is detected in step 171, calibration values are calculated and stored for later use in the analysis of measured attributes of other slides 102 through 108. After the storage of the calibrate values in step 173, the flow proceeds to a step 172 to determine if all slides have been analyzed in step 172. Since in the present example, they have not, the slide holder is moved to position the objective in the rectangle 87 of the next slide in the slide set, which is slide 102. In the present example, slides 102 through 108 will be analyzed in sequence in the same manner as calibrate slide 101, except that the data measured in their specimen portions 88 is not stored as calibrate data but as analysis results.

When the last slide 108 has been completely analyzed, the flow diagram of FIGS. 9 and 10 is terminated and the accumulated analysis result data is available for reports as described in detail in the aforementioned U.S. Pat. No. 5,008,185 to Bacus.

In the preceding embodiment, the cell samples were automatically located by the apparatus during an analysis operation. In order to speed analysis times, the apparatus 10 can be used to preselect points on the slide where analysis is to occur. The apparatus 10 includes the interactive optical means 11a which comprises the microscope 12 having multiple turret objectives including a low power objective. The microscope 12 has mounted thereon a manually operable stage for carrying a microscope slide having a biological specimen thereon. The manually operable stage may be manipulated by the operator to bring various portions of the slide under the low power microscope objective. When the operator finds a region of interest, that region is located by the position sensors 12a which are disclosed in U.S. Pat. No. 5,018,209 to Bacus, the content of which is incorporated herein by reference, may be marked by a press of a button 15 on the mouse, keyboard or the like to signal the processor means that the coordinates of that field are to be stored so that the field may later be examined at high power by the automatic optical means 11b. Thus, the slide may be quickly and rapidly scanned manually at low power selecting the portions of interest and then loaded into the slide rack 62a with other slides for examination at high power by objective 64a using the high speed automatic processing as set forth previously. The low magnification scan of interactive system 11a allows empty fields and fields which are not of interest to be avoided to reduce the amount of time consumed by the automatic optical means 11b. The system 10 therefore provides the advantage of the combination of interactive, rapid, low power scanning and storage of coordinates with high power automatic assay for full diagnostic treatment of the biological specimen.

Further, after the high power assay has been completed, the images may be called up from the WORM drive 45 for additional editing or for deletion from assays, statistics and the like. Thus, the system allows pre-assay editing of the fields by the use of the low power microscope and post-assay editing of the fields with re-assaying by calling up the images from the WORM drive 45.

In the preceding description, the tray of slides 62a could be placed in the automatic optical apparatus 116 and the individual slides, e.g., 101, would be searched for calibrate and specimen samples, which samples would be appropriately analyzed. Additionally, the slides could be previewed under a low power microscope 12 and locations of analysis interest entered directly into the analysis apparatus 10 to identify the starting points of analysis functions.

A third method and apparatus can also be employed to identify search locations on microscope slides. The third method and apparatus, which is described in detail below, permits the selection of a plurality of search locations, called action points, on each of the plurality of slides in a slide tray, e.g., 62a, and permits the operator to specify an action e.g., scan or set light, at each selected action point. The action points and associated actions are easily selected interactively with the analysis apparatus 10 in preparation for an analysis session. Advantageously, the action points and associated actions can be selected on other ancillary apparatus and a data file representing such selections can be prepared. When analysis is to occur, the slide tray is loaded into the automatic optical apparatus 11b and a corresponding data file is entered into the analysis apparatus 10 by moveable storage means (diskette) or electronic communication.

Figure 14A:
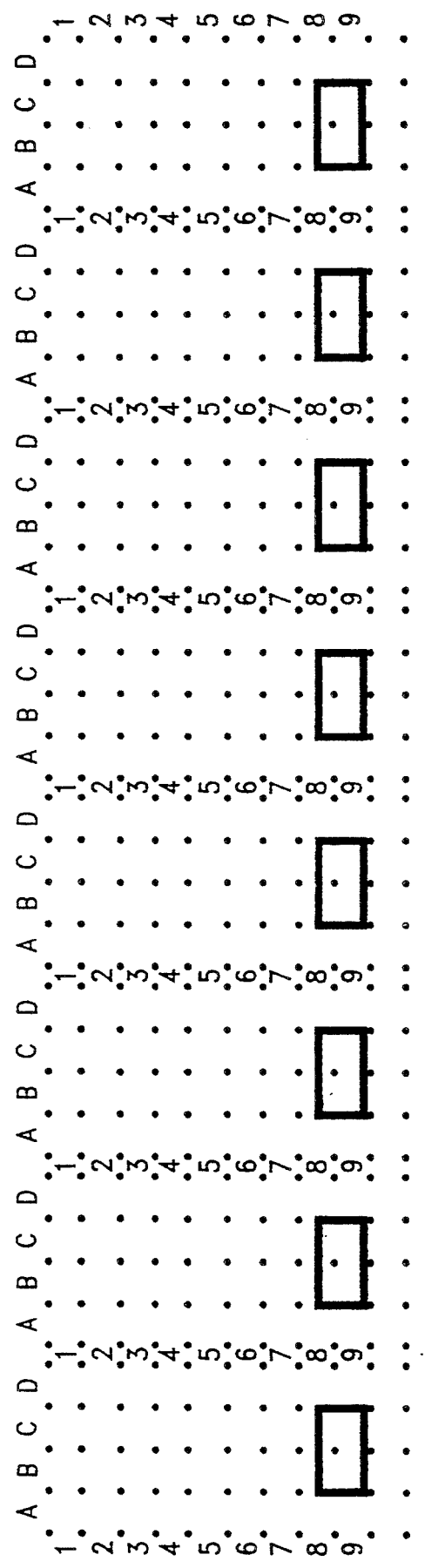
FIG. 14a is a template for use in identifying slide action points.
Figure 14B:
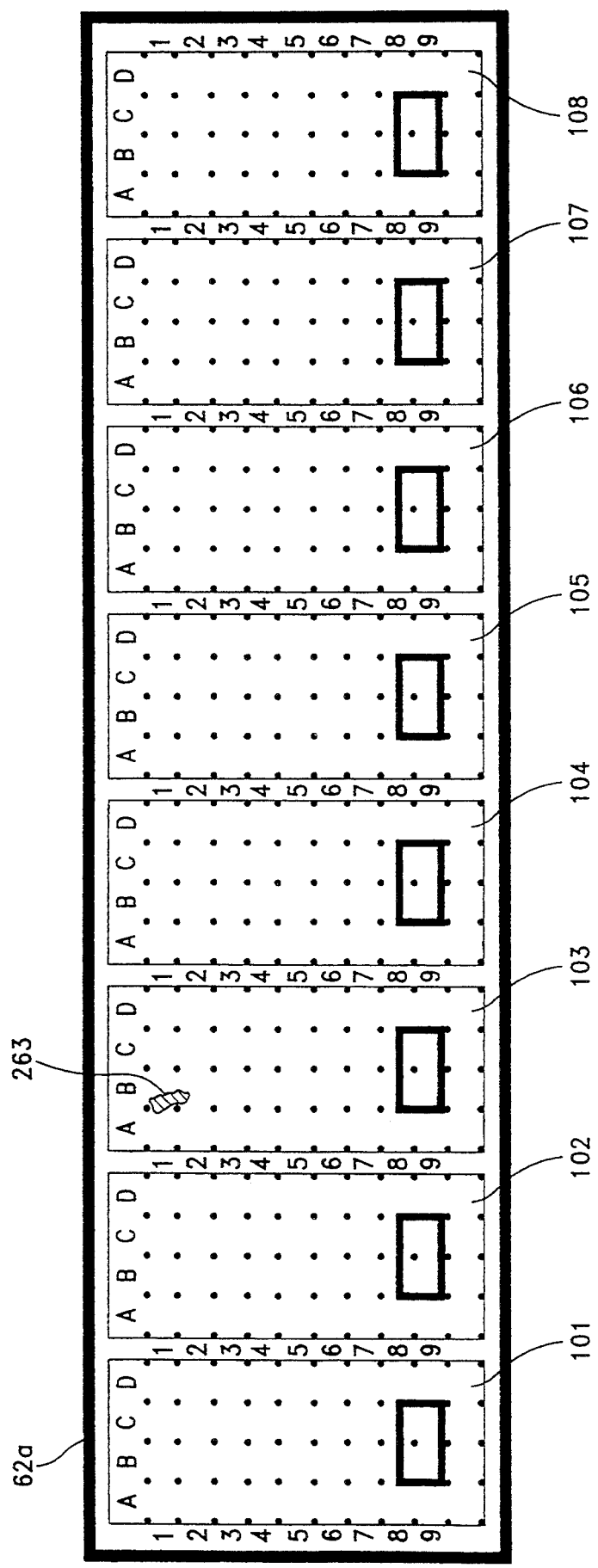
FIG. 14b is a representation of a slide tray in which the template of FIG. 14a is visible.
Figure 15:
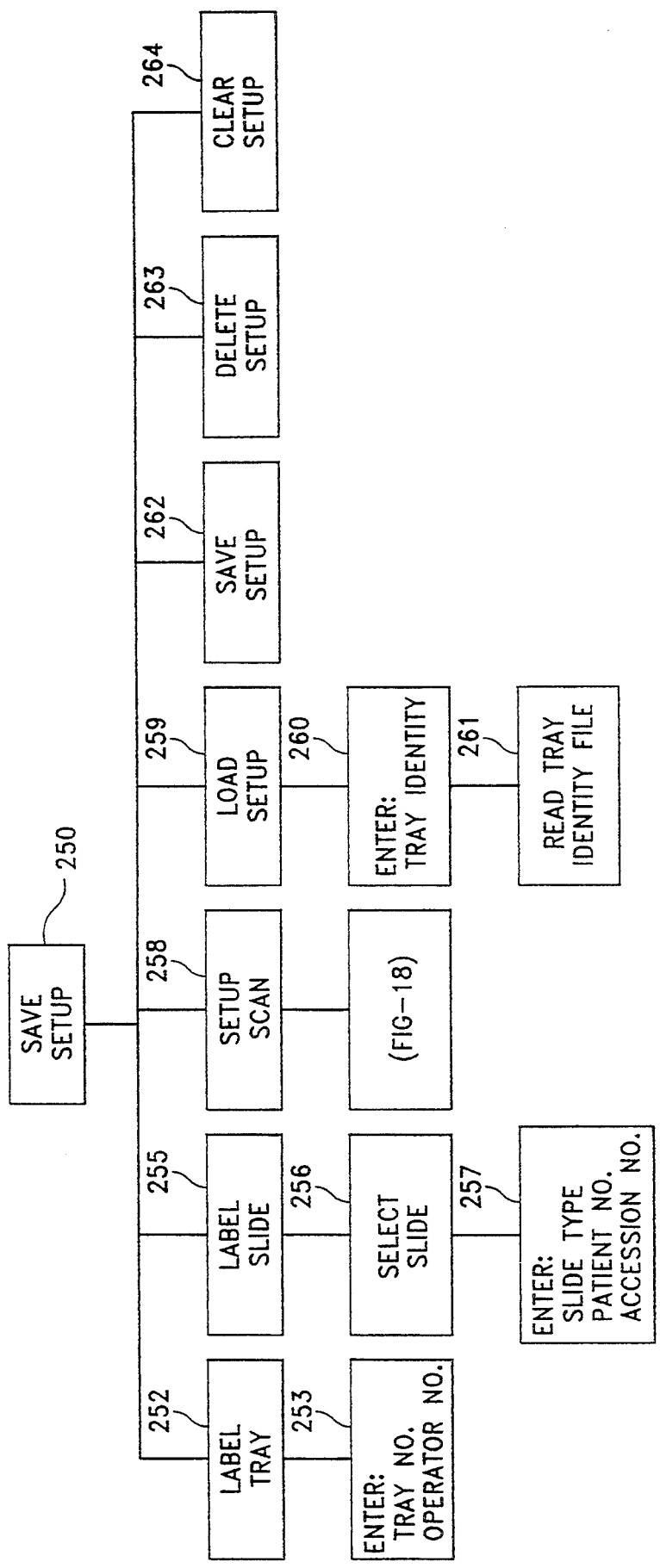
FIG. 15 shows the apparatus operations available from a tray setup function of the apparatus.

The selection of action points begins after at least one slide is mounted in a slide carrier (slide tray) 62a and involves visual inspection of the slides by an operator and entry of information by that operator into the computer 32 by means of keyboard 56 and mouse 13. When the slides have been loaded into the slide tray 62a, the tray is placed over a coordinate grid-forming template 251 as shown in FIG. 14a and a tray setup function 250 (FIG. 15) is initiated on the analysis apparatus 10. FIG. 14b shows a slide tray 62a held so that the coordinate grid of the template 251 is formed on the slides. The template 251 and slide tray 62a may be held in position by an appropriate jig (not shown). In the present embodiment, the slide tray 62a is positioned over the gridded template which is viewed through the slides. Other methods of forming a grid reference on the slides could be used, such as projecting the grid on the slides by optic means or viewing the slides through a clear gridded template.

The tray setup function includes operator reviewing of its actual slides 101 through 108, a determination of the locations of points of interest (action points) on the slides from the coordinate pattern and the entry into apparatus 10 of information defining the points of interest. The tray setup function 250 begins with a visual image 270 (FIG. 16) of a slide tray and slides 273 being displayed on instruction monitor 52. Also displayed on monitor 52 in the tray setup step function 250 is a tray setup menu 272, which identifies routines to be performed. The individual routines of menu 272 are selected by moving a cursor 271 by means of mouse 13 and selecting a routine by pressing the button 15 when the cursor is on a routine. The selection of menu items by means of a mouse and cursor is well known in the art. The routines available in the tray setup function 250 are also shown in flow diagram form in FIG. 15.

Initially, the label tray routine 252 is entered to establish the identity of the slide tray being set up for analysis. In the label tray routine 252, the instruction monitor displays a window shown at 253 of FIG. 15, requesting entry by the operator of a preassigned tray identity number and a pre-assigned operator number. Upon exiting from the label tray routine by operator selection, the routine returns to the tray setup function 250 and establishes a tray data file 280 (FIG. 17) for the identified tray. The data file 280 is stored in RAM 38 at a location identified by the tray identity number. The tray data file 280 includes a tray header 281 which stores both the tray identity number and the operator identity number as entered by the operator.

Figure 16:
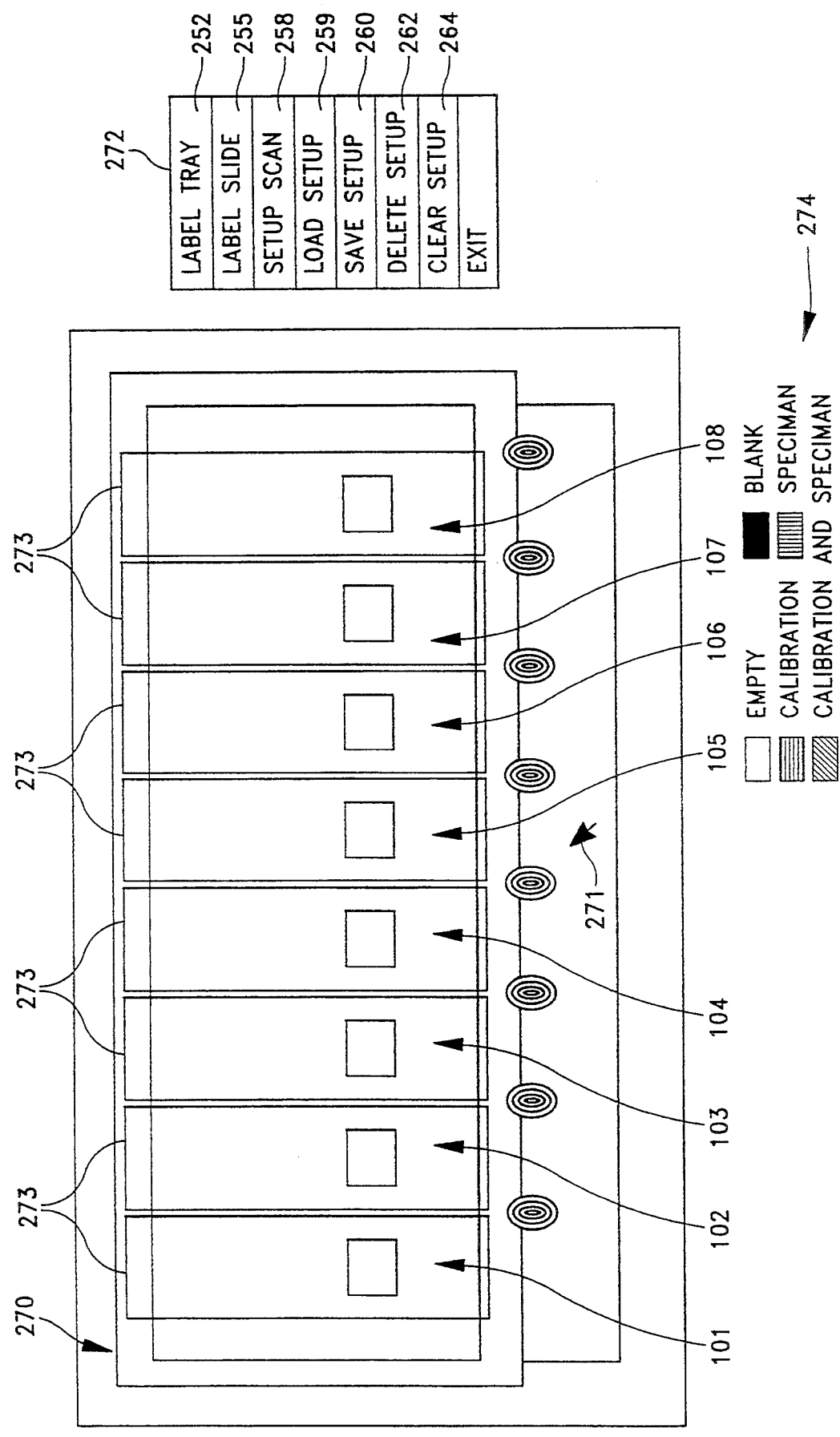
FIG. 16 is a visual image presented to an operator during the tray setup functions.
Figure 17:
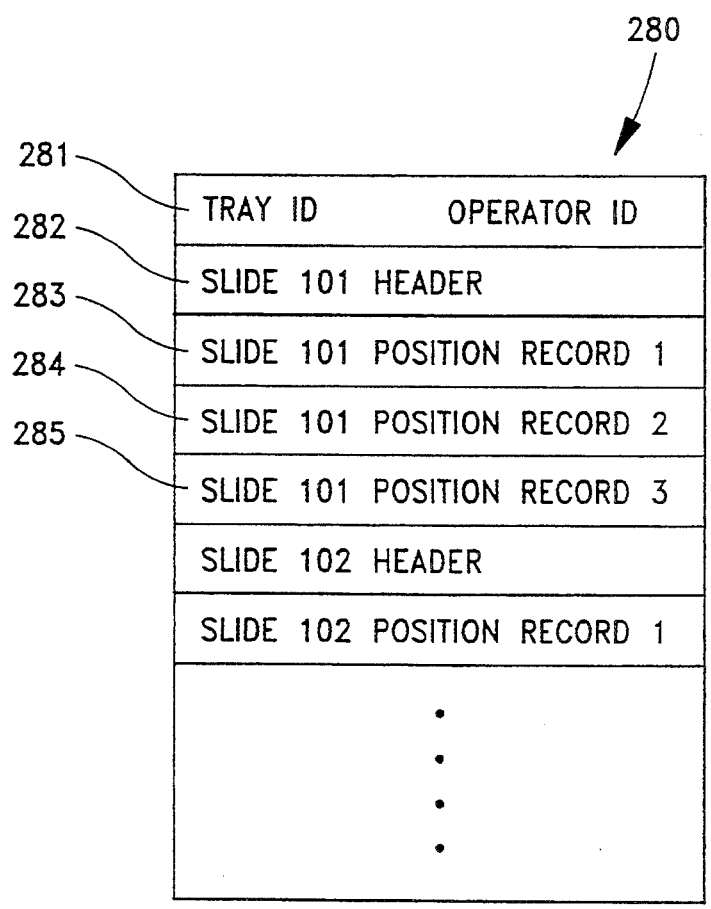
FIG. 17 shows a data file established during tray setup.

After the flow returns to the tray setup function 250, the operator selects the label slide routine 255. In the label slide routine 255, the operator selects from the displayed slide tray one of the slide images 273 which corresponds to an actual slide in the slide tray being set up. The slide image 273 is selected by the mouse 13 and cursor 271. Upon selecting a slide image, a prompt appears on monitor 52 for operator entry of the type of slide being set up, the patient number for the slide and the accession number. The prompt is represented at step 257 in FIG. 15. The slide types are shown at 274 in FIG. 16. When the data requested in step 257 has been entered, the routine returns to the tray setup function 250 which stores the entered data in a slide header 282 of data structure 280 (FIG. 17). The label slide routine 255 can be used to identify all 8 slides in the tray which resulting in the storage of 8 slide headers, each associated with one slide 101–108. In FIG. 16, the actual slide numbers from slides 101–108 have been written in parenthesis on slides 273 to show the correspondence between actual slides and slide images.

Figure 18:
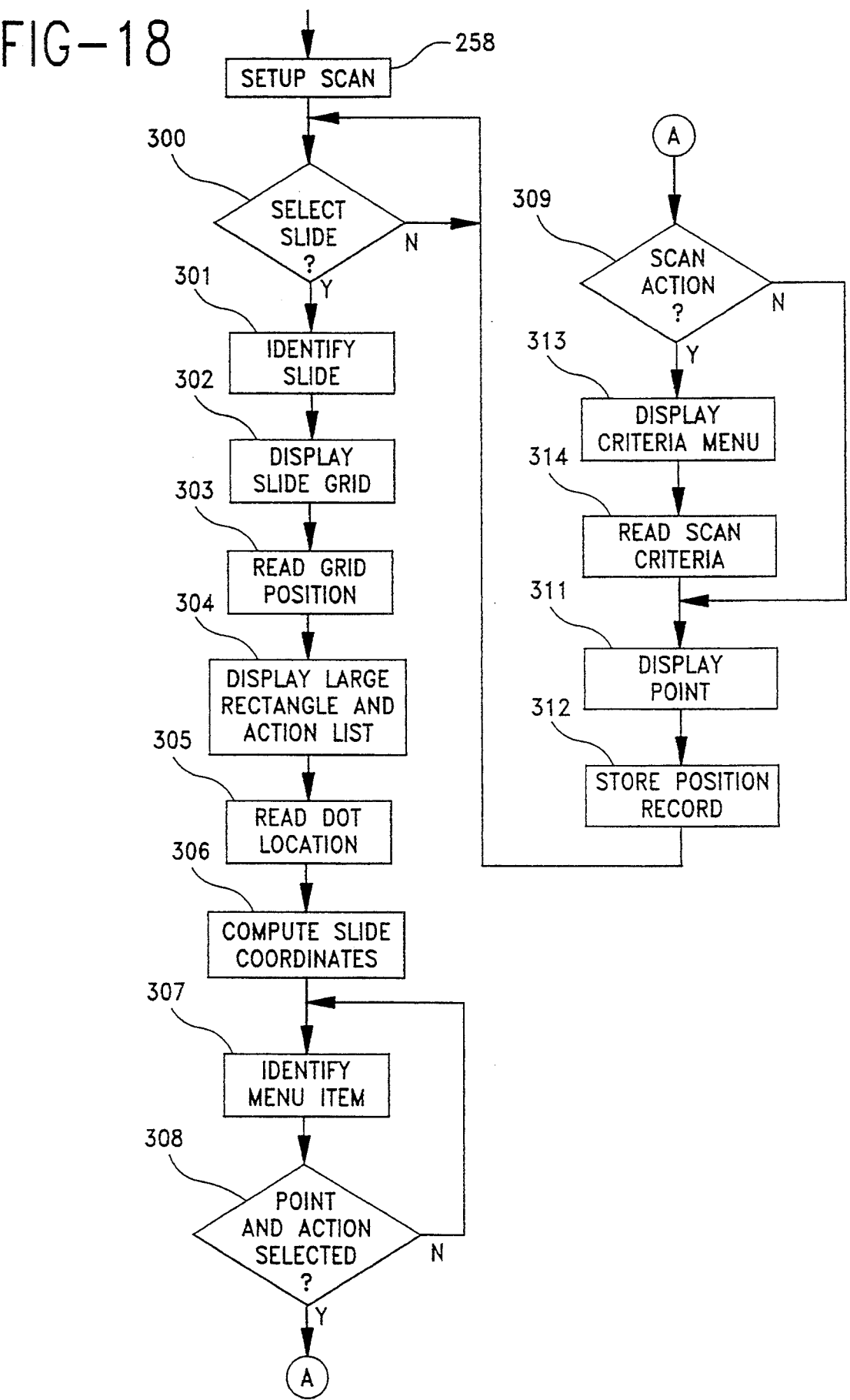
FIG. 18 is a flow diagram of a setup scan routine.

After the slide images 273 have been labelled in routine 255, the operator selects the setup scan routine 258 from menu 272. The setup scan routine allows the operator to identify action points on the slides and to define an action to be performed at each identified action point. A flow diagram of the setup scan routine 258 is shown in FIG. 18. In the setup scan routine 258, the operator first selects a slide image 273 by cursor 271 movement. When a slide image 273 has been selected (step 300), the flow proceeds to a step 301 where the identity of the actual slide 103 corresponding to the selected slide image is read. Next, a step 302 is performed in which a slide grid 276 (FIG. 19), is displayed on monitor 52. Slide grid 276 is an enlarged image of the selected slide image and includes a reference grid pattern of four columns labelled A through D and nine rows, labelled 1 through 9. The rectangles represented in slide grid 276 correspond to the pattern of reference rectangles formed on the actual slides in the slide tray 62a, as shown in FIG. 14b. When the operator wants to specify a particular point on the actual slide for analysis or other action, he or she selects the rectangle on slide grid 276 which includes the particular point. Since the grid rectangles on the slide grid 276 correspond to the reference rectangles formed on the slides held in the slide holder (FIG. 14b), the identification of a rectangle of interest on slide grid 276 is a relatively simple task.

As represented in FIG. 14b, a portion of a cell sample is present in rectangle B-1 of slide 103. Accordingly, the operator moves cursor 271 to the rectangle B-1 of slide grid 276 on monitor 52 and presses button 15 to select rectangle B-1. The rectangle position is read by the apparatus 10 at step 303 (FIG. 18) and the flow proceeds to a step 304, where a large grid 277 and an action menu 278 are displayed on monitor 2. Large grid 277 represents the selected rectangle B-1 of slide grid 276, and allows precise positioning of an action point within the selected rectangle. The large grid 277 is sub-divided into, for example, 100 horizontal (X) by 100 vertical (Y) coordinate positions one of which can be selected by moving the tip of cursor 271 thereto and pressing mouse button 15. A dot 279 is shown in the lower left-hand quadrant of large grid 277 to represent a selected point in cell sample 263. The X, Y coordinate position of point 279 in large grid 277 is read by the apparatus in step 305. Since the position of rectangle B-1 on the slide is predetermined and its position of point 279 within rectangle B-1 is now known, the absolute X, Y coordinate of the point on the slide is computed and stored in step 306.

Each action point selected is associated with one of the actions listed in menu 278. Accordingly, the operator next moves the cursor to menu 278 to select one of the menu items. The selected action which is identified in step 307 is used in a manner described below to control apparatus 10 during the analysis of the slides on the slide tray. That is, after all slides have been appropriately "marked" with action points, each associated with an action, the slide tray is mounted in automated assay apparatus 11b as shown in FIGS. 1 and 1a and the apparatus 10 implements the specified actions at the specified action points. It is important to note that the actions do not take place when selected but are recorded in a data file, e.g., 280, for use after the slide tray 62a is placed in assay apparatus 11b.

Figure 19:
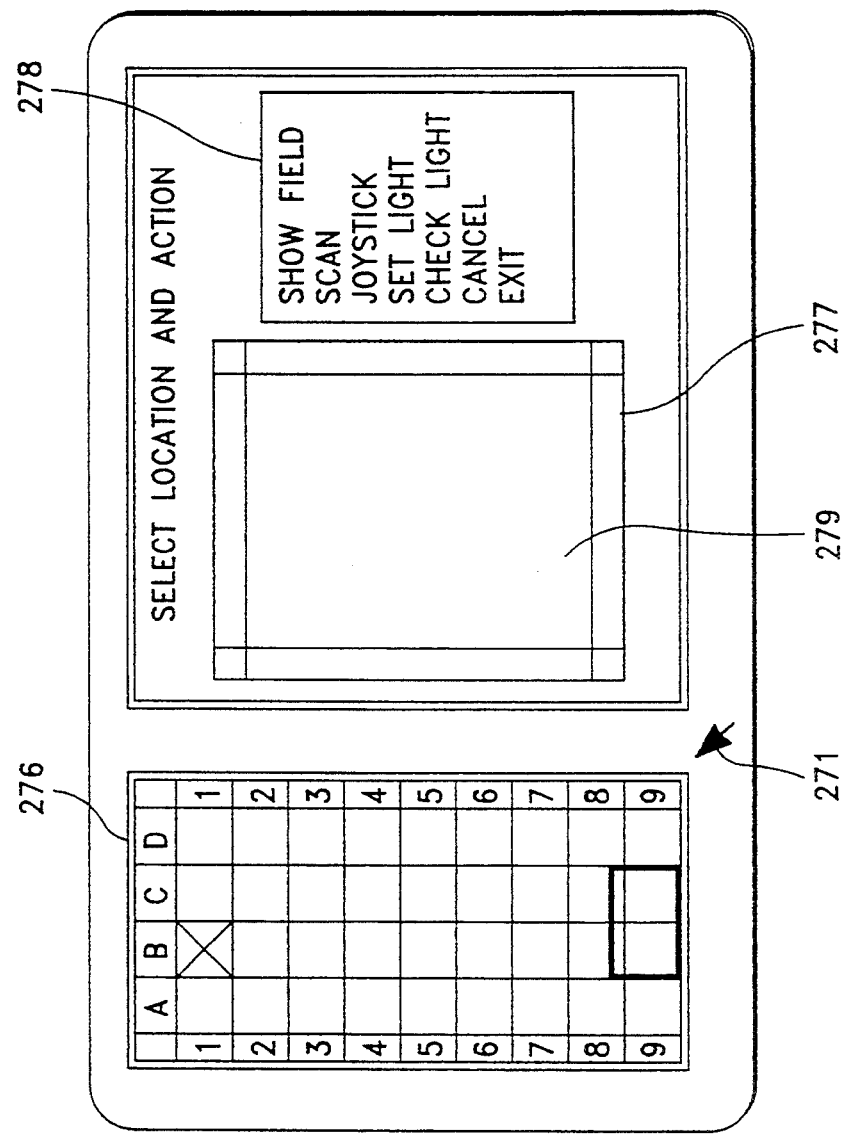
FIG. 19 shows a monitor screen displayed during tray setup.

The following briefly describes the actions listed in menu 278 of FIG. 19. The show field action will cause the apparatus 11b to align the specified action point with objective lens 64a and display a focused image field of the action point on image monitor 30. The joystick action will cause the apparatus to align the specified action point with the objective lens 64a and to release the control of the alignment between the objective 64a and the microscope slide to the operator, through joystick 13a manipulation. The set and check light actions also cause the apparatus to properly align the specified action point with the objective lens 64a, at which point light levels can be set or checked respectively, as previously discussed. The scan action will cause the alignment of the microscope objective 64a and the selected action point on a microscope slide and then begin to measure the attributes of a sample on the microscope slide. In the present embodiment, the scan action requires additional information to define the measurements to be made and how the scan is to be performed. The accumulation of such additional information is described later herein.

A step 308 (FIG. 18) is performed to detect the selection of both an action point and its associated action. Subsequently, a check 309 is made to determine if the selected action is a scan action. Flow proceeds to step 311, when the selected action is not a scan action. In step 311, a dot 279 is displayed on monitor 52 image 270 to indicate the position of the newly selected action point. Next, a step 312 is performed to store in data file 280 the accumulated data, called a position record, identifying the coordinate address of the action point and its associated action. For non-scan actions, the position record comprises data representing the location of the selected action point and the associated action. The position record is stored in association with the slide header, e.g., 282 of the slide identified in step 301. In data file 280 (FIG. 17), the position records 283, 284 and 285 associated with slide 101 are shown occupying memory locations subsequent to the slide 101 header 282. It should be noted the other forms of association such as linking or address translation tables could be used to associate slide headers with their associated position records. Advantageously, multiple position records can be associated with the same slide.

When the performance of step 309 detects that a scan action has been selected, the flow moves to step 313 in which a scan criteria menu 279 (FIG. 20) is displayed on instruction monitor 52. The scan criteria menu 279 in conjunction with mouse and keyboard manipulation by the operator, defines the parameters of the scan to be performed at a previously selected action point. The scan type menu item 286 can be selected to set the scan-type to raster (as shown), horizontal or vertical. Raster scanning is a zig-zag pattern, as shown in FIG. 5, horizontal scanning consists of a straight line across the slide and vertical scanning consists of a straight line along the slide length. The X and Y step rate menu items 288 and 289 can be selected and set to define the spacing between evaluated image fields. Similarly, the definitions of blank fields and good fields (fields of analysis value) can be established by selecting and setting menu items 290 and 291.

The sample type menu item 293, allows the operator to specify whether the sample being evaluated is a specimen or a calibration sample. Specifying the sample type identifies how the measured cell object attributes in the image fields are to be evaluated when the slide is later analyzed in the apparatus 11b. The scan criteria menu 279 also includes a settable value 295 to identify the end of a scan line. As shown in menu 279, an end of line has been set to occur when three consecutive blank image fields are viewed. Menu 279 also includes a settable value 296 which terminates a raster scan at a preset number of zig-zags and a settable value 297 which terminates a scan when a set number of image fields have been analyzed.

After the scan criteria have been set using the scan criteria menu 279, the operator exits from the menu and the apparatus reads, at step 314, the established scan criteria values. From step 314, flow proceeds to block 311 where the action points are displayed on the slide tray image 270, as previously described. Flow proceeds through step 312, in which the position record is stored in data file 280, to the select slide step 300. It should be mentioned that for scan actions, the position record stored in data file 280 includes the scan defining criteria established in menu 279 in addition to the action point coordinates and specified action, e.g., scan. At the conclusion of the setup scan routine 258, flow returns to the tray setup function 250 of FIG. 15.

Four additional routines are available from the tray setup function 250. A load setup routine 259 responds to the operator entry (step 260) of a slide tray identity, for which a data file was previously created, by reading (step 261) the identified slide tray data file. A save setup routine 262 commits a just-prepared data file 280 to a more secure memory storage, for example, into disk storage. A clear setup routine 264 permits the clearing of the most recently created setup data file before it is committed to the more secure storage. A delete setup routine 263 enables the deletion of an identified data file from the more secure memory area.

After the completion of the slide tray setup function 250, a slide tray data file 280 as represented in FIG. 17 exists in memory. The slide tray data file 280 is accessible by its tray identity number and includes data representations of one or more action points, each in association with one of the described actions.

Figure 21:
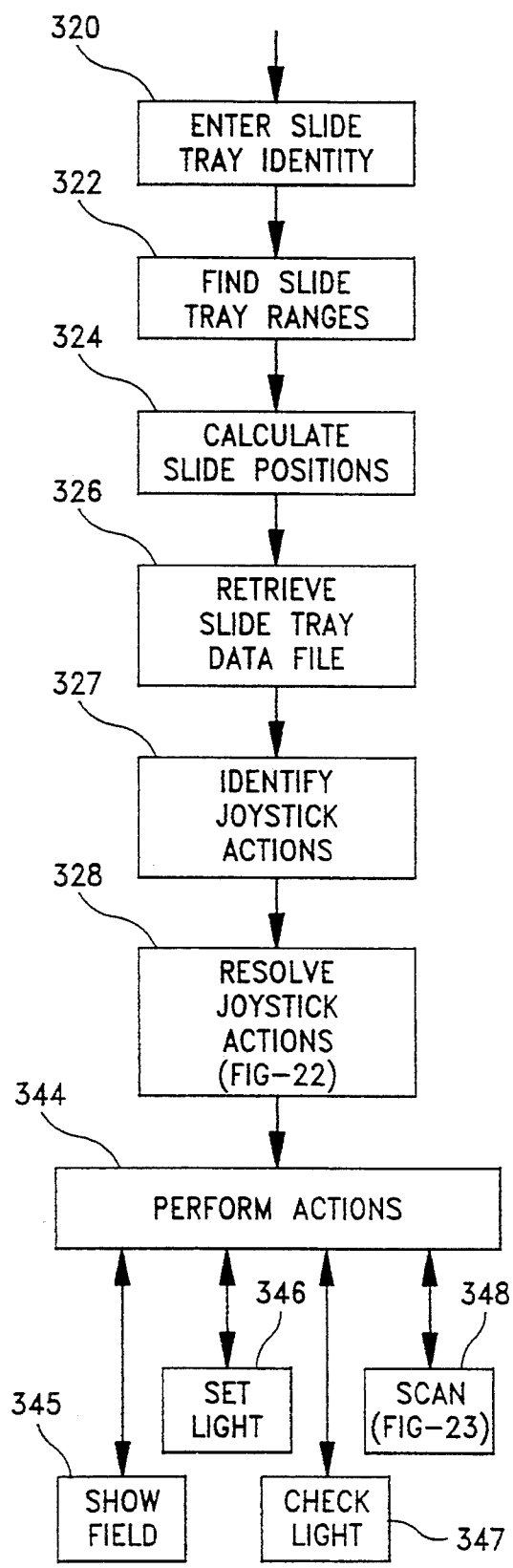
FIG. 21 is a flow diagram of analysis by the apparatus after slide locations have been selected.

FIG. 21 is a flow diagram of the steps performed by apparatus 10 in the analysis of biological specimens mounted on the slides of the identified slide tray. The preceding actions establish a data file 280 identifying action points and actions for a slide tray identified by an identity number. When the slide tray is to be analyzed, it is loaded into automated assay processing system 11b of apparatus 10 and the slide tray identity of the loaded slide tray is entered (step 320) at keyboard 56. Initially, the slide tray ranges are found in step 322 and slide positions calculated in step 324 in the manner described above with regard to the flow diagram of FIG. 9. Then, in response to the entered slide tray identity, the computer 32 retrieves (step 326) the slide tray data file identified by the slide tray identity entered in step 320. Next, a step 327 is performed in which the position records of all slides are read from the slide tray data file 280 and reviewed to identify all action points associated with joystick actions. The joystick actions are separated from the other actions because they involve continued operator activity.

Figure 22:
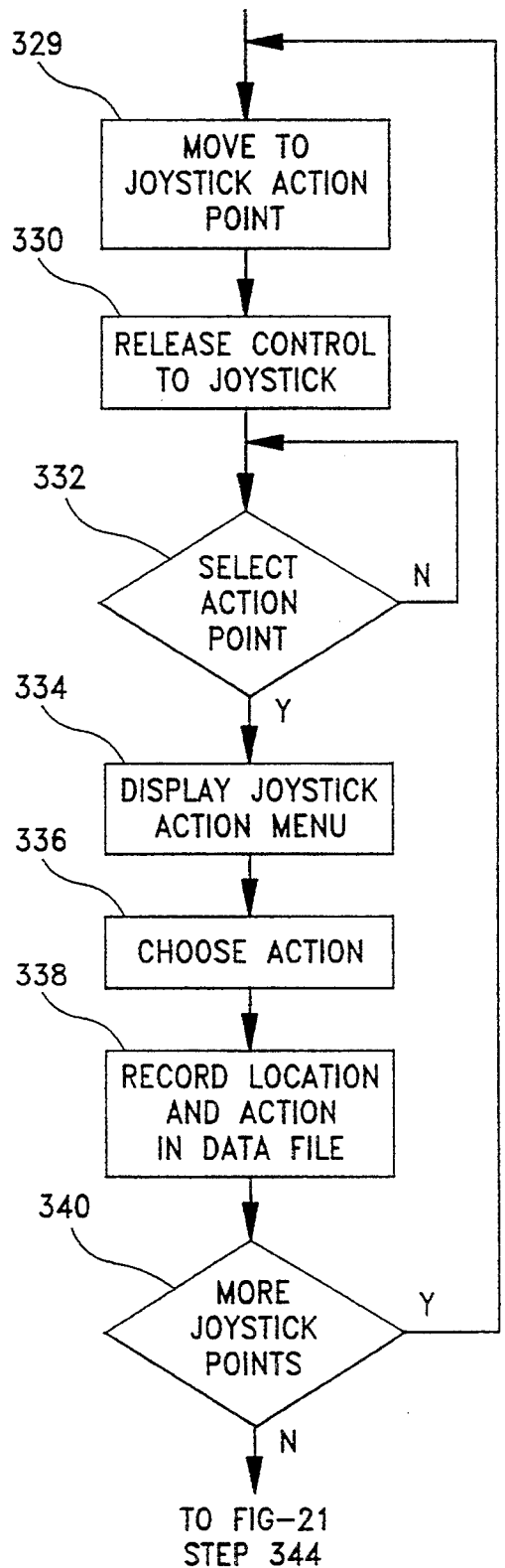
FIG. 22 is a flow diagram of operations performed to resolve joystick actions.

FIG. 22 is a flow diagram of the joystick completion routine 328. Initially, the slide tray is moved (step 329) by the automated assay system 11b to align the first joystick action point with the microscope objective 64a. After routine focusing, the image field at the action point is presented on display monitor 30 and the X-Y position control of the slide tray 62a is released to the joystick (step 330). While the joystick 13a is in slide position control, the computer 32 responds to joystick signals by controlling the assay processing system 11b to move the slide to positions determined by operator interaction with the joystick 13a. When the operator finds, by observing the image on display monitor 30, an image field at which an action is desired, the mouse button 15 is pressed. The pressing of button 15 is detected in step 332. The pressing of the mouse button 15, while under joystick 13a control, establishes the image field present when the button is pressed as an action point. In response to the press of mouse button 15, an action selection menu is displayed on instruction monitor 52 in step 334. This action selection menu is substantially identical to action selection menu 278 of FIG. 19. The mouse 13 is used to select in step 336 one of the listed actions for association with the action point then represented on display monitor 30. Upon selection of the action, a position record is created and stored (step 338) in the slide tray data file 280 (FIG. 17). After the new position record is stored in the data file, the list of joystick actions is checked in step 340 to determine if further joystick actions are present. When additional joystick actions are present, the flow returns to step 329 to perform again the above-described sequence. Alternatively, when no joystick actions remain, the flow proceeds to action step 344 in which the performance of the actions now specified in slide tray data file 280 are performed.

Figure 23:
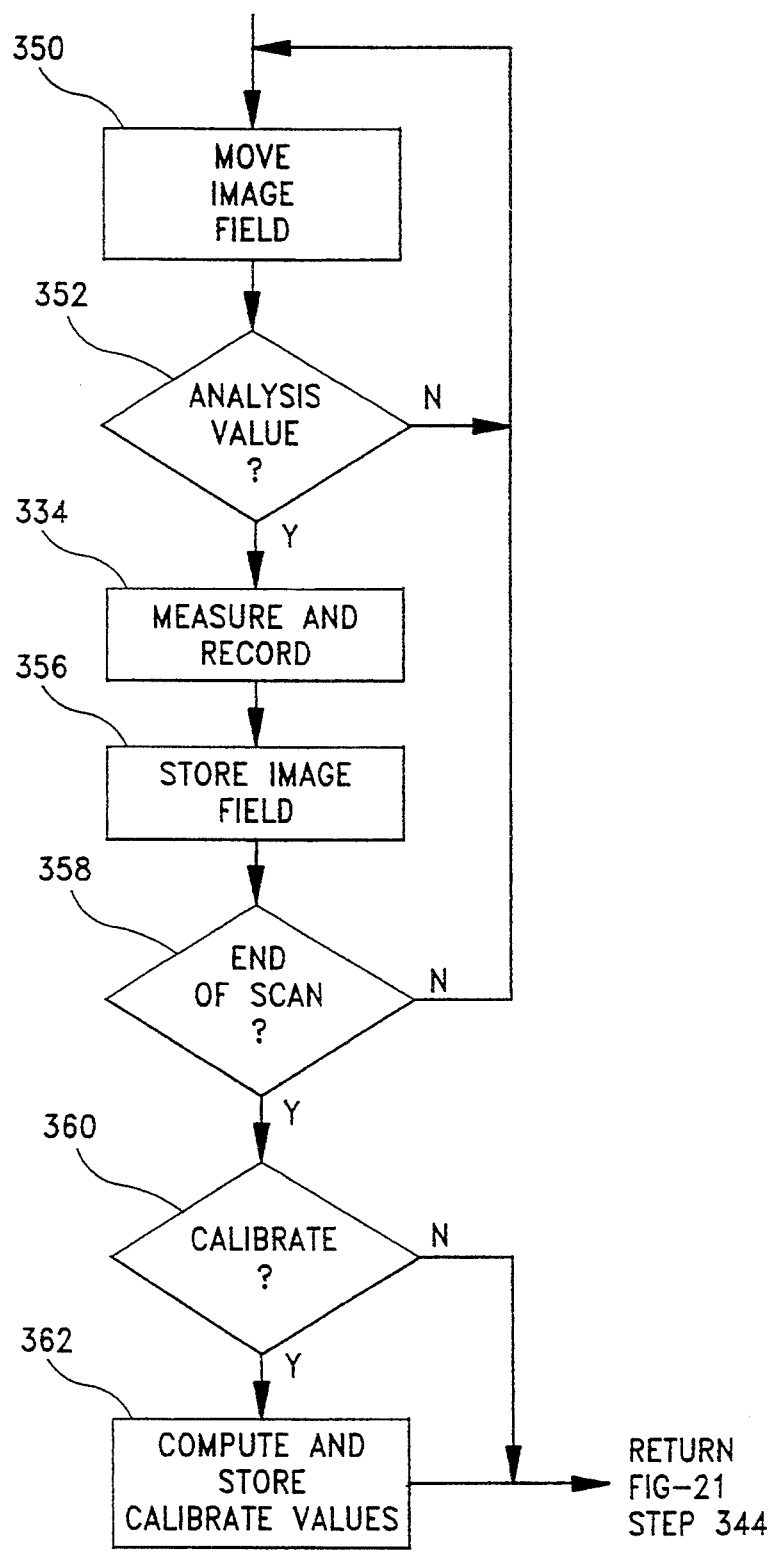
FIG. 23 is a flow diagram of a scan routine.

In action step 344, the slide headers e.g., 282 (FIG. 17) are reviewed in sequence from slide 101 through slide 108 to identify slides to be analyzed. When a slide header for a slide to be analyzed is accessed, its associated position records are accessed in sequence to control the operation of the analysis apparatus. In response to each position record in slide tray data file 280, the objective 64a is substantially aligned with the action point defined in the position record, and the associated action stored in the position record is performed. When the action is a show field action 345, the assay processing system 11b is controlled to present the image at the action point to display monitor 30 and to record a copy of the image. After such recording, flow returns to the action step 344 for the analysis of another position record. When a position record includes a set light or check light action, the set 346 or check light 347 function respectively is performed after movement of the apparatus to the action point defined in the position record. The remaining action type is performed through action function 344 is the scan action 348, which is shown in greater detail in FIG. 23.

The scan action begins at step 350, in which the slide tray 62a is controlled to move the image field at the selected action point to microscope objective 64a. As previously discussed, the field is focused after each move operation. The image field at the action point is then analyzed in step 352 to determine whether the image field has analysis value. The scan criteria of the present position record is consulted to determine the definition of a good field. For example, in the scan criteria represented in the menu 279 (FIG. 20) a good field is one in which 70% of its area comprises cell objects. When the image field does not have analysis value, the flow returns to block 350 where the slide tray is moved to place a new image field under objective 64a. The type of move operation performed is controlled by the previously established scan type, X step rate and Y step rate stored in the position record type for the present action point. For example, if the scan type is set to vertical scanning and the Y step rate to 2 apparatus 11b would be controlled to move in the Y direction by two fields and stop to image a new field. After the new image field is focused, it is again analyzed in step 352 for a determination of its value for analysis. When the analysis value step 352 determines that the current image field has analysis value, flow proceeds to step 354 where the attributes of the cell objects in the image field are measured and recorded. Next a pixel image of the current image field is stored in bulk data storage in step 356 and a step 358 is performed to determine if the end of the scan has been reached. The end of scan criteria are stored along with other scan criteria in the current position record. When the end of scan has not been reached, flow returns to step 350 from which a new image field is found and analyzed. When step 358 determines that the end of scan has been reached, a step 360 is performed to determine the sample type of the cell objects being analyzed. If the sample type is a calibrate sample, the calibrate values are computed and stored in a step 362 and the flow returns to the action step 344. Alternatively, when step 360 determines that a specimen sample has been scanned, flow returns directly to the action step 344. When in action step 344, the computer 32 again reviews the slide tray data file to identify additional, unserviced position records. Action step 344 will service these unserviced position records until all have been serviced. At which time, a message is displayed on instruction monitor 52 which indicates the completion of the present analysis operation.

Figure 20:
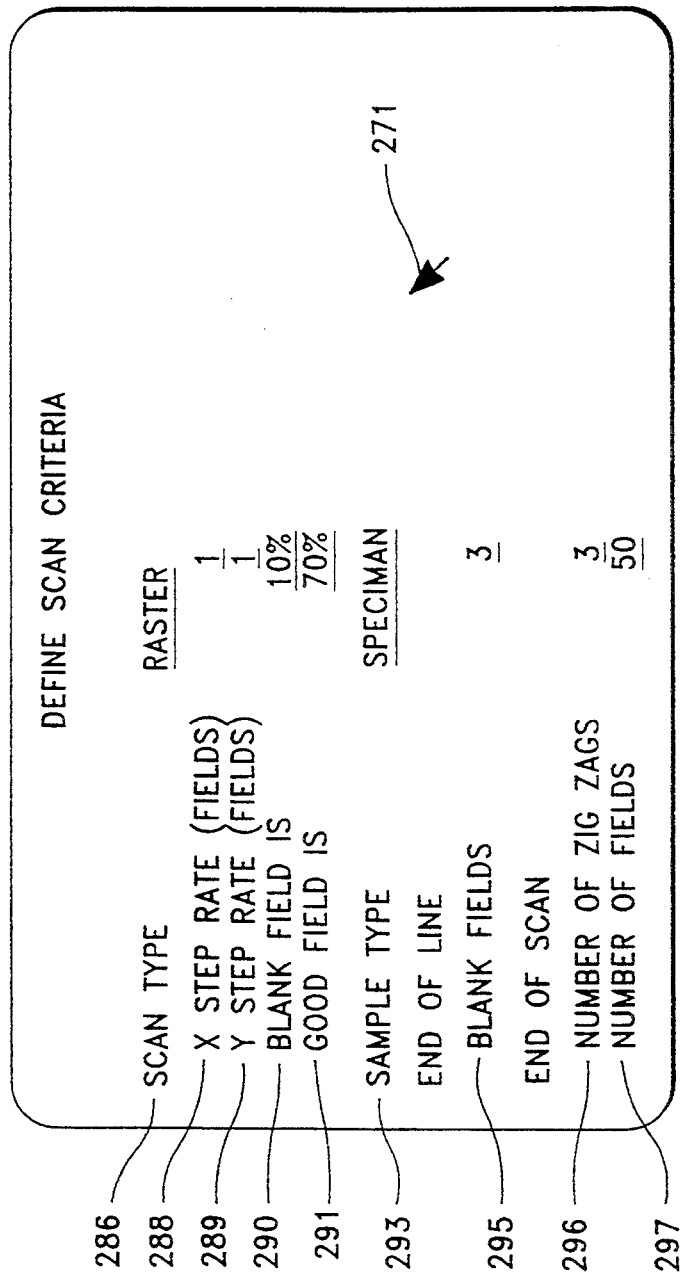
FIG. 20 shows a monitor screen displayed during a setup scan routine.

In the preceding embodiment, the operator enters a sample type during the setting of scan criteria (FIG. 20). As specifically disclosed, the sample type is either specimen or calibrate. Other choices of sample type could also be available without departing from the invention. For example, the type of assay such as DNA mass assay or red blood cell hemoglobin assay, could be set as sample types and the apparatus 10 could analyze the measured and recorded attributes accordingly. Also, each slide in a slide tray could include different types of cell samples such as blood cells or tumor cells prepared in a manner specific to that type of cell sample. In such situations, the operator would enter the cell type during the label slide routine 255. The analysis apparatus would then read the sample type from the slide header, e.g., 282 to cause the appropriate analysis routines to be executed.

The disclosed embodiments present an automated biological specimen analysis method and apparatus. Improvements are disclosed which permit an operator to preselect action points on one or more slides. The automated apparatus responds to the preselected action points by moving directly to them without the inefficiencies of a search routine. Advantageously, an action point pre-selection embodiment includes the ability to specify and record an action to be performed at each action point. Certain actions have been specifically disclosed, however, persons of ordinary skill in the art may include other actions without departing from the invention. Additionally, the disclosed embodiments use display monitors and menus for data entry. Other types of data entry could be used without departing from the invention.

While there has been illustrated and described a particular embodiment of the present invention, it will be appreciated that numerous changes and modifications will occur to those skilled in the art, and it is intended in the appended claims to cover all those changes and modifications which fall within the true spirit and scope of the present invention.

What is claimed is:

1. A method for locating a small biological specimen on a large specimen area of a transparent slide for later automated analysis of the specimen, said method comprising the steps of:

providing a slide before an operator for viewing at low resolution at a first microscope so that the operator may rapidly exclude areas on the slide and proceed to locate an action point on a small specimen at the low resolution of a first magnification with a first microscope; and viewing the slide at the low resolution and locating the action point in the section associated with the specimen, and storing the location as a coordinate address; automatic scanning beginning at the coordinate address and progressing automatically through a plurality of image fields at a substantially higher magnification and resolution with a second microscope than the low resolution.

2. A method in accordance with claim 1 including the additional steps of:

providing the slide with a reference grid to divide the slide into a plurality of designated grid sections, and selecting one of the designated grid sections having specimen for viewing at the low resolution.

3. A method in accordance with claim 1 in which the step of storing the location of said specimen includes the steps of moving a mark on a monitor screen to the location of the specimen and then entering the address of the mark for initiating subsequent automatic scanning of a plurality of image fields.

4. A method in accordance with claim 1 including the additional steps of noting a previously placed mark on the slide adjacent the specimen made by a pathologist and entering the coordinate address of this previously placed mark as the address to initiate scanning at the substantially higher resolution.

5. A method in accordance with claim 1 including the step of providing a flat bed carrier and positioning the slide in the flat bed carrier with a plurality of other slides and positioning the carrier and each slide at its associated stored coordinate address to locate specimens for each of the slides to facilitate subsequent automatic scanning of a plurality of image fields of each of the slides.

6. A method of analysis of biological specimens on each of a plurality of slides having large specimen areas with a specimen occupying only a small fraction of the specimen area, said method comprising the steps of:

providing a plurality of specimen locating stations at which an operator locates the small specimen in the large specimen area;

providing a specimen carrier at each station for the operator to handle a plurality of slides associated with the carrier;

the operator at each station viewing a specimen slide at low resolution and the operator storing the location of the specimen on a storage media;

transferring the slides and their carrier to an automated analysis station;

transferring the stored locations of the addresses of the specimens to the analysis station;

initiating scanning of the specimens at a substantially higher resolution than the low resolution at the location address previously established by the operator; and automatically positioning each of the slides beneath the microscope of a digital imaging apparatus for an automated analysis thereof using the previously applied addresses to avoid scanning large areas empty of the specimen to be scanned.

7. A method in accordance with claim 6 including the shifting of a flat bed carrier having a plurality of slides in front of the operator.

8. A method in accordance with claim 7 including the steps of the operator designating regions on the specimen area at a first low resolution, enlarging the designated region on the slide to show the specimen enlarged, and then noting the address to initiate scanning.

9. An interactive method of specifying one or more action points on each of a group of microscope slides mounted in a carrier for subsequent automatic image analysis comprising:

positioning a slide mounted in the carrier before an operator who visually inspects the slide to select the coordinate locations of one or more action points on the slide;

entering into storage the coordinate address of at least one action point;

selecting and entering into storage one or more appropriate actions for subsequent automatic image analysis at said at least one action point;

providing a group of slides in the carrier;

proceeding to each of the group of slides in the carrier and having the operator visually inspect each slide to select one or more action points and having the operator enter the coordinate location for each action point into storage;

forming an enlarged image on a monitor related to the location of the action point and the operator entering from the enlarged image a more finely defined coordinate address for a given action point into storage;

displaying on a monitor an image of a microscope slide having a coordinate grid pattern of rectangles thereon; and forming a coordinate grid on at least one of the microscope slides and the operator using a display cursor to locate the action point on the monitor grid related to the location of the action point on the slide.

10. A method in accordance with claim 9 including the selecting with the cursor one of the displayed grid rectangles and then enlarging that grid rectangle for viewing on a monitor and using a spot locator to select a location spot within the enlarged grid rectangle on the monitor as the coordinate location of the action point.

11. A method of assaying with a microscope and an image analysis means of biological specimens on each of a group of microscope slides mounted in a carrier comprising:

positioning a slide before an operator who visually inspects the slide for one or more action points on the slide with a first microscope at a first resolution and selects a coordinate address on the slide for the action point;

entering into storage the address for the action point and a selected function from one of several functions performable at the various action points;

proceeding to each of the slides of the group of slides in the carrier and having the operator view each of the slides, the operator entering the coordinate address and selected analysis action for each action point into storage;

positioning the carrier with the slides therein into an operative position with respect to a second microscope at the image analysis means and at a higher resolution; and reading each of the stored addresses for each of the slides and automatically moving the carrier relative to the second microscope to position each stored address on each slide at the microscope for performing automatically the action for that action point by the image analysis means.

12. A method in accordance with claim 11 including:

displaying an enlarged image on a monitor related to the location of the action point and the operator entering from the enlarged image a more finely defined coordinate address for a given action point into storage.

13. A method in accordance with claim 12 including the steps of locating an action point for light calibration and locating an action point for analysis of specimen cells.

14. A method in accordance with claim 13 including the forming of a grid on the slide and for the operator viewing a grid displayed on the monitor from storage, the operator using a cursor to locate the address point on the grid on the monitor related to the location of the action point on the slide.

15. A method in accordance with claim 14 including the selecting with the cursor one of the grid areas and then enlarging that grid area for viewing on a monitor and using a spot locator to select a location spot within the enlarged grid area on the monitor as the coordinate address of the action point.

16. An apparatus for interactively specifying one or more action points on each of a group of microscope slides, said apparatus comprising:

means for holding the group of slides in a side-by-side relationship before an operator who visually inspects the slides for one or more action points on each slide;

means for providing an associated visible coordinate system for the slide to allow an operator to select a coordinate address on the slide for each action point;

a monitor to display the visible coordinate system with respect to a slide at the operative position;

a storage means for storing addresses of selected action points on the slide;

means for displaying an enlarged image on the monitor related to the location of the action point at a resolution substantially lower than the resolution at which said action point is subsequently analyzed; and means for generating a spot on the enlarged image and thereby to produce a more finely defined coordinate address for a given action point;

wherein said visible coordinate system is provided by means for generating a grid pattern on the slide for viewing by the operator, and wherein said apparatus includes a monitor having a grid displayed from storage, a monitor cursor to locate the address point on the grid on the monitor related to the location of the action point on the slide.

17. An apparatus in accordance with claim 16 including means for producing from storage an enlarged view of a grid area on the monitor and a spot generator to selected a location spot within the enlarged grid area on the monitor as the coordinate address.

18. An apparatus for assaying biological specimens on each of a group of microscope slides, said apparatus comprising:

means for holding a slide before an operator who visually inspects the slide for one or more action points on the slide;

means providing an associated coordinate system for the slide to allow an operator to select a coordinate address on the slide for the action point;

a storage means for storing in the storage means address and associated analysis action for each slide;

means for entering into storage the address and a selected analysis action from one of several analysis actions performable at the various action points;

said means for holding slide, holding the next slide of the group of slides in the carrier for viewing the next slide and an associated coordinate system provided therewith and selecting an action point thereon, said means for entering being operable by the operator to enter the coordinate address and selected analysis action for each action point into storage;

an image analysis means for receiving a carrier with the slides therein into an operative position;

a microscope in the image analysis means for viewing a slide at the operative position;

means for automatically moving the carrier relative to the microscope to position each stored address on each slide at the microscope operative position for performing the associated stored analysis action for that action point by the image analysis means;

a monitor to display the coordinate system with respect to a slide at the operative position;

means for forming an enlarged image on the monitor related to the location of the action point;

means for generating a spot on the enlarged image and thereby to produce a more finely defined coordinate address for a given point; and means for generating a grid pattern on the slide for viewing by the operator, said monitor having a grid displayed from storage, and a cursor to locate the address point on the grid on the monitor related to the location of the action point on the slide.

19. An apparatus in accordance with claim 18 in which the image analysis means includes means for performing a light calibration action at one addressed action point on a slide and means for analyzing specimen cells at another addressed action point on a slide.

20. An apparatus in accordance with claim 18 including means for producing from storage an enlarged view of a grid area on the monitor and a spot generator to select a location spot within the enlarged grid area on the monitor as the coordinate address of an action point.

21. An apparatus for automated assay of biological specimens positioned on microscope slides comprising:

a first microscope of a first resolution for viewing action points on a microscope slide;

specifying means actuated by an operator for specifying at least one action point on a microscope slide by an operator;

selecting means operated by an operator for selecting an analysis action from one of several actions performable by said automated apparatus to be performed at each action point specified by the specifying means;

means operable by said specifying means and selecting means for storing associated representations of the location of each specified action point and each defined action to be performed at the specified action point for subsequent automatic analysis;

means for reading a specified action point representation and the defined action representation associated therewith from the storage means; and automatic analysis means including a second microscope having a microscope objective at a higher resolution, for aligning said microscope objective with each action point represented by the action point representation read from said storage means and for performing the action represented by the action representation associated therewith.

22. An apparatus in accordance with claim 21 wherein said means for specifying comprises display means for displaying a visual image of portions of a microscope slide;

means responsive to operator interaction for moving a cursor on said displayed visual image; and means for selecting an action location identified by said cursor.

23. An apparatus in accordance with claim 22 wherein said display means displays location reference markings on the displayed visual image.

24. An automated apparatus in accordance with claim 23 comprising means for forming on the microscope slide a visual pattern of location reference markings substantially identical to the pattern of reference markings displayed on said displayed visual image.

25. An apparatus in accordance with claim 22 wherein said display means displays a pattern of grid markings defining a plurality of rectangles on said displayed visual image, and said means for specifying comprises means for specifying one of said rectangles.

26. An automated apparatus in accordance with claim 25 comprising means for forming on the microscope slide a pattern of grid markings substantially identical to the grid markings presented on said displayed visual image.

27. An apparatus in accordance with claim 21 wherein said means for defining comprises display means for displaying a plurality of possible actions;

means responsive to operator interaction for moving a cursor on the displayed plurality of actions; and means for selecting one of said plurality of actions identified by said cursor.

28. An automated apparatus in accordance with claim 22 comprising means for displaying indicia of an identified action point on said displayed visual image of portions of a microscope slide.

29. An apparatus in accordance with claim 21 wherein one of said definable actions comprises a scan action and said means for defining actions comprises means for accumulating information identifying a type of analysis to be performed from a plurality of types of analysis performable by said automatic analysis means, and said means for storing, stores the information identifying the type of analysis in association with a specified action point.

30. An apparatus in accordance with claim 29 wherein said type of analysis includes an estrogen/progesterone assay.

31. An apparatus in accordance with claim 29 wherein said type of analysis includes a DNA mass assay.

32. An apparatus in accordance with claim 21 wherein one of said definable actions comprises a scan action, said means for defining an action comprises means for accumulating information describing a pattern of scan movements between said microscope slide and said microscope objective, and said means for storing stores the information describing the pattern of scan movements in association with a specified action point.

33. An automated apparatus for identifying action points for the performance of analysis functions on biological specimens positioned on microscope slides comprising;

means operable manually by an operator for specifying by operator interaction at least one action point address on a microscope slide;

means operable manually by an operator for selecting an analysis action from one of several actions performable by said automated apparatus to be performed at each action point address specified by the operator operating said means for specifying;

means for storing in a data file associated representations of each specified action point address and each defined action to be performed at the specified action point;

means for transmitting to a separate image analysis apparatus said data file for performance of said specified actions;

means responsive to operator interaction for moving a cursor on said displayed visual image;

means for selecting an action point identified by said cursor;

wherein said display means displays location reference markings on the displayed visual image; and means for forming on the microscope slide a visual pattern of location reference markings substantially identical to the pattern of reference markings on said displayed visual image.

34. An automated apparatus for identifying action points for the performance of analysis functions on biological specimens positioned on microscope slides comprising:

means operable manually by an operator for specifying by operator interaction at least one action point address on a microscope slide;

means operable manually by an operator for selecting an analysis action from one of several actions performable by said automated apparatus to be performed at each action point address specified by the operator operating said means for selecting;

means for storing in a data file associated representations of each specified action point address and each defined action to be performed at the specified action point;

means for transmitting separate image analysis apparatus said data file for performance of said specified actions;

means responsive to operator interaction for moving a cursor on said displayed visual image;

means for selecting an action point identified by said cursor;

wherein said display means displays a pattern of grid markings defining a plurality of rectangles on said displayed visual image, and said means for specifying comprises means for specifying one of said rectangles; and means for forming on the microscope slide a pattern of grid markings substantially identical to the grid markings presented on said displayed visual image.

35. An apparatus in accordance with claim 34 wherein said means for defining comprises display means for displaying a plurality of possible actions;

means responsive to operator interaction for moving a cursor on the displayed plurality of actions; and means for selecting one of said plurality of actions identified by said cursor.

36. A method in accordance with claim 2 and wherein the low resolution at which the slide is viewed provides an enlarged view of the grid section.

37. A method in accordance with claim 2 wherein the slide is viewed without magnification when selecting one of the designated grid sections having specimen.

38. An apparatus in accordance with claim 33 wherein said means for defining comprises display means for displaying a plurality of possible actions;

means responsive to operator interaction for moving a cursor on the displayed plurality of actions; and means for selecting one of said plurality of actions identified by said cursor.

* * * * *